United States Patent [19]

Harada et al.

[11] Patent Number: 4,723,004
[45] Date of Patent: Feb. 2, 1988

[54] CEPHEM COMPOUNDS

[75] Inventors: Setsuo Harada, Kawanishi; Shigetoshi Tsubotani, Suita; Hideo Ono, Kobe, all of Japan

[73] Assignee: Takeda Chemical Industries, Ltd., Osaka, Japan

[21] Appl. No.: 681,784

[22] Filed: Dec. 14, 1984

[30] Foreign Application Priority Data

Jan. 23, 1984 [JP] Japan .................................. 59-10856
Aug. 24, 1984 [JP] Japan .................................. 59-177293
Sep. 18, 1984 [JP] Japan .................................. 59-195985

[51] Int. Cl.$^4$ ................. C07D 501/08; A61K 31/545
[52] U.S. Cl. ..................................... 540/221; 435/119
[58] Field of Search ........................... 544/21; 514/201; 540/225, 221, 224

[56] References Cited

U.S. PATENT DOCUMENTS

| 4,555,363 | 11/1985 | Milner | 260/239.1 A |
| 4,587,333 | 5/1986 | Ono et al. | 540/221 |
| 4,667,027 | 5/1987 | Harada et al. | 540/221 |

FOREIGN PATENT DOCUMENTS

| 155405 | 8/1984 | European Pat. Off. |
| 114752 | 8/1984 | European Pat. Off. |
| 114750 | 8/1984 | European Pat. Off. |
| 137489 | 8/1984 | Japan |
| 172492 | 9/1984 | Japan |
| 172494 | 9/1984 | Japan |
| 2107307 | 4/1983 | United Kingdom |

OTHER PUBLICATIONS

Vogel, A Textbook of Organic Chemistry pp. 1072–1073 (1956).
The Journal of Antibiotics, vol. 37, No. 7, pp. 773–780 (1984).
Program and Abstracts of the Twenty-Fourth Interscience Conference on Antimicrobial Agents and Chemotherapy, p. 292 (1984), No. 1139.

Primary Examiner—Nicholas S. Rizzo
Attorney, Agent, or Firm—Wenderoth, Lind & Ponack

[57] ABSTRACT

A compound of the formula:

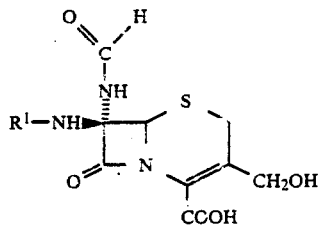

wherein $R^1$ is

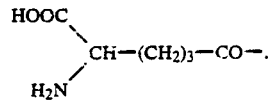

HOOC—(CH$_2$)$_3$—CO— or hydrogen, or a salt thereof, is useful as an intermediate for the production of cephem compounds, and some of them are useful as antimicrobial agents.

4 Claims, 8 Drawing Figures

CEPHEM COMPOUNDS

The present invention relates to cephem compounds and their production.

The present inventors isolated a large number of microorganisms from soil and plants and found that a certain microorganism is able to produce novel cephem antibiotics. The inventors named these antibiotics TAN-547, TAN-592 and TAN-591. TAN-547 is composed of at least six components TAN-547 A, B, C, D, E and F, TAN-592 is composed of at least six components TAN-592 A, B, C, D, E and F, and TAN-591 is composed of at least three components TAN-591 A, B and C. Furthermore, the present inventors found that when TAN-547 A, B or C, TAN-592 A, B or C, or TAN-591 A, B or C is subjected to hydrolysis, 7-formylaminocephem compounds are obtained, and that when TAN-547 D, E or F or TAN-592 D, E or F is subjected to hydrolysis, deacetylcephalosporin C is obtained, and further 7-formylamino-cephem compound is converted to 7-formylamino-7-amino-cephem compound by enzymatic reactions.

The present inventors conducted further research based on these findings, and have completed the present invention.

The present invention is directed to:

(1) A compound of the formula:

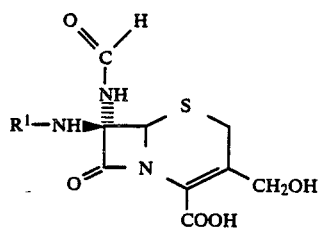

wherein $R^1$ is

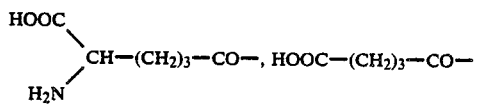

$HOOC-(CH_2)_3-CO-$ or hydrogen, or a salt thereof.

(2) A method for producing a compound of the formula:

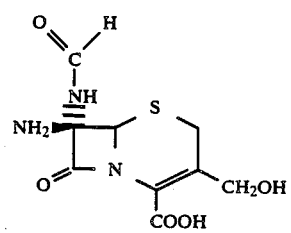

or its salt, which comprises contacting a compound of the formula:

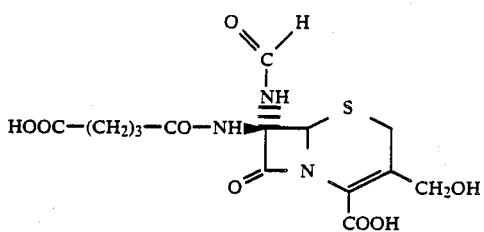

or its salt, with a culture broth or a processed matter of a culture broth of a microorganism which belongs to the genus Pseudomonas and is capable of converting the group $HOOC-(CH_2)_3-CO-NH-$ at 7-position of the starting material to the group $NH_2-$, (3) A method for producing a compound (III) or its salt, which comprises contacting a compound of the formula:

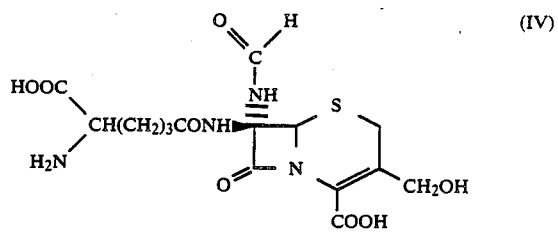

or its salt, with a culture broth or a processed matter of a culture broth of a microorganism which belongs to the genus Trigonopsis and is capable of converting the group

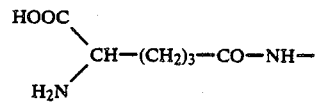

at 7-position of the starting compound to the group $HOOC-(CH_2)_3-CO-NH-$, and (4) A method for producing a compound (IV), deacetylcephalosporin C or its salt, which comprises subjecting a compound of the formula:

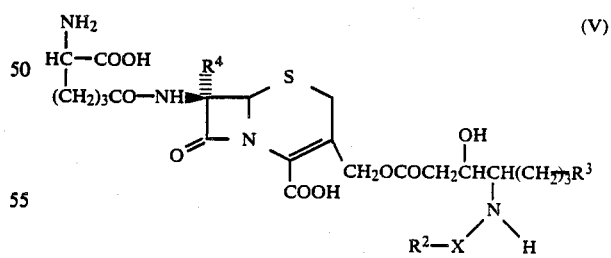

wherein $R^4$ is formylamino or hydrogen, $R^2$ is one or two of residue(s) of amino acid or peptide selected from the group consisting of serine and alanine or hydrogen, $R^3$ is $-NH-C(=NH)-NH_2$ or $-CH_2NH_2$ or X is a residue of alanine or serine; provided that when X is a residue of alanine, $R^2$ is one or two of residue(s) of amino acid or peptide of alanine or hydrogen and $R^3$ is $-NH-C(=NH)-NH_2$, or its salt, to hydrolysis.

In the above formula, a residue of alanine represents

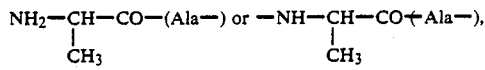

a residue of serine represents

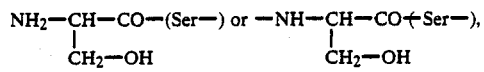

and formylamino represents

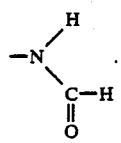

In the present specification, the compounds shown by the formula (V) are named as follows:

| Antibiotic | —R⁴ | X | R²— | —R³ |
|---|---|---|---|---|
| TAN-547A | —NH—CHO | —Ala— | H— | —NH—C(=NH)—NH₂ |
| TAN-547B | —NH—CHO | —Ala— | Ala— | —NH—C(=NH)—NH₂ |
| TAN-547C | —NH—CHO | —Ala— | Ala—Ala— | —NH—C(=NH)—NH₂ |
| TAN-547D | —H | —Ala— | H— | —NH—C(=NH)—NH₂ |
| TAN-547E | —H | —Ala— | Ala— | —NH—C(=NH)—NH₂ |
| TAN-547F | —H | —Ala— | Ala—Ala— | —NH—C(=NH)—NH₂ |
| TAN-592A | —NH—CHO | —Ser— | H— | —NH—C(=NH)—NH₂ |
| TAN-592B | —NH—CHO | —Ser— | Ser— | —NH—C(=NH)—NH₂ |
| TAN-592C | —NH—CHO | —Ser— | Ala—Ser— | —NH—C(=NH)—NH₂ |
| TAN-592D | —H | —Ser— | H— | —NH—C(=NH)—NH₂ |
| TAN-592E | —H | —Ser— | Ser— | —NH—C(=NH)—NH₂ |
| TAN-592F | —H | —Ser— | Ala—Ser— | —NH—C(=NH)—NH₂ |
| TAN-591A | —NH—CHO | —Ser— | H— | —CH₂—NH₂ |
| TAN-591B | —NH—CHO | —Ser— | Ser— | —CH₂—NH₂ |
| TAN-591C | —NH—CHO | —Ser— | Ala—Ser— | —CH₂—NH₂ |

The term Antibiotic TAN-547 or TAN-547 will be sometimes used in order to refer to the individual Antibiotic TAN-547 A, B, C, D, E or F, or a mixture containing at least two of them. The term Antibiotic TAN-592 or TAN-592 will be sometimes used in order to refer to the individual Antibiotic TAN-592 A, B, C, D, E or F, or a mixture containing at least two of them. The term Antibiotic TAN-591 or TAN-591 will be sometimes used in order to refer to the individual Antibiotic TAN-591 A, B or C, or a mixture containing at least two of them.

In this specification, 7-formylamino-deacetylcephalosporin C i.e. compound (IV) and deacetylcephalosporin C are on some occasions referred to briefly as "7-FA-DCPC" and "DCPC", respectively.

Salts of the above compounds, in cases in which they are used as pharmaceuticals, such as a therapeutic agent for bacterial infections, include for example pharmaceutically acceptable salts, such as lithium salt, sodium salt, barium salt, calcium salt and magnesium salt, and in the case of their being utilized as a synthetic intermediate, include for example the above-mentioned salts as well as ammonium salt, methylamine salt, diethylamine salt, trimethylamine salt, tetrabutylammonium salt and pyridine salt.

The starting material Antibiotics TAN-547, 592 and 591 can be produced by cultivating in a culture medium a microorganism which belongs to the genus Lysobacter or Xanthomonas and is capable of elaborating Antibiotic TAN-547, 592 or 591, respectively, to have said antibiotic produced and accumulated in the culture broth and harvesting the Antibiotic TAN-547, 592 and 591, respectively.

As examples of the microorganisms which produce TAN-547, 592 or 591, *Lysobacter lactamgenus* YK-90, *Xanthomonas lactamgena* YK-280 and *Xanthomonas lactamgena* YK-278 are mentioned. These microorganisms have been deposited at Institute for Fermentation (IFO), Japan, and at the Fermentation Research Institute, Agency of Industrial Science and Technology, Ministry of International Trade and Industry (FRI), Japan, and the deposits have been converted to deposits under the Budapest Treaty and have been stored at FRI.

The following is the accession numbers and deposit dates of the microorganisms.

| Microorganism | IFO Accession number, Deposit date | FRI Accession number, Deposit date | Accession number under the Budapest Treaty |
|---|---|---|---|
| *Lysobacter lactamgenus* YK-90 | IFO 14288 September 14, 1983 | FERM P-7247 September 19, 1983 | FERM BP-575 |
| *Xanthomonas lactamgena* YK-280 | IFO 14330 March 20, 1984 | FERM P-7602 April 28, 1984 | FERM BP-635 |
| *Xanthomonas lactamgena* YK-278 | IFO 14351 June 18, 1984 | FERM P-7681 June 25, 1984 | FERM BP-636 |

The process for the production of the compound (IV) or DCPC from the compound (V) is carried out by treating the starting compound under alkaline conditions. Such alkaline conditions include aqueous solutions having a pH adjusted to about 7 to 11, preferably about 9 to 9.7, to which the starting compound is added for treatment.

The said aqueous solutions include, for example, buffers being normally used in the chemical reactions, and as the said buffers, there may be mentioned for example aqueous solutions adjusted to the above pH range with phosphates, borates, citrates, carbonates, hydrochlorides, acetates, sodium hydroxide, glycine, veronal, borax, ammonium salts, aminomethylpropane diol, and the like.

The hydrolysis reaction in the present invention is carried out by allowing the reaction to proceed at a temperature of about 0° to 80° C., preferably about 20° C. to 40° C., for about 1 hour to 72 hours, preferably about 4 hours to 40 hours.

In the method for producing the compound (III) from the compound (IV), any microorganism, which belongs to the genus Trigonopsis and capable of converting the compound (IV) to the compound (III), is employed. As the microorganism, one which belongs to the species *Trigonopsis variabilis* is mentioned. Specific examples of the microorganism used are exemplified by *Trigonopsis variabilis* IFO 0671 and IFO 0755.

The microorganisms identified by the IFO numbers has been deposited at IFO, Japan and are listed in IFO List of Cultures 1984 seventh edition. The following is the deposit dates of the microorganisms to the IFO.

| Microorganism | Deposit date |
|---|---|
| IFO 0671 | October 29, 1954 |
| IFO 0755 | October 15, 1955 |

The morphological characteristics of the microorganism, *Trigonopsis variabilis*, is identical with those described in Yeasts; A Taxonomic Study, 1970, second edition, pages 1353–1937, Editor: J. Ladder, Publisher North Holland Pub Corporation.

In the method for producing the compound (II) from the compound (III), any microorganism, which belongs to the genus Pseudomonas and capable of converting the compound (III) to the compound (II), is employed. As an example of the microorganism employed, there may be mentioned Pseudomonas sp. UK-2221, which was isolated from soil samples collected in Fukuchiyama City, Hyogo Prefecture, Japan.

The microbiological characteristics of Strain UK-2221 are described in the following:

(a) Morphology:

Observation after the cultivation on a nutrient-agar slant at 24° C. for 5 days reveals that the cells are in the form of rod having a diameter of 0.5 to 1.0 $\mu$m and a length of 0.8 to 2.0 $\mu$m; and that the microorganism, with flagella observed, forms no spore, and is gram-negative but not acid-fast.

(b) The growth characteristics on various media:

Observation was made during the cultivation at 24° C. over the period of 1 to 14 days.

(1) Nutrient-agar plate culture: Colorless and circular colonies with convex round surface and entire edge. No diffusible pigment produced.

(2) Nutrient-agar slant culture: Moderate growth. Colorless colonies. No diffusible pigment produced.

(3) Nutrient broth culture: Poor turbid growth. Sediments formed. No membranous growth.

(4) Nutrient-gelatin stab culture: Slight growth. No liquefaction activity.

(5) Litmus milk: No reduction ability. No peptonization activity.

(c) Physiological properties:

(1) Reduction of nitrates: —

(2) Denitrification reaction: —

(3) MR (methyl Red) test: —

(4) VP (Voges-Proskauer) test: —

(5) Production of indole: —

(6) Production of hydrogen sulfide (lead-acetate-paper): —

(7) Hydrolysis of starch: —

(8) Utilization of citric acid (Koser's, Christensen's and Simmons' culture media): + (Simmon's media —)

(9) Utilization of nitrogen source (I) Potassium nitrate: +

(II) Ammonium sulfate: +

(10) Production of pigments (King A and B and mannitol-yeast extract-agar culture media): No production of diffusible pigment observed.

King A culture medium: 10 g of glycerol, 20 g of peptone, 1.4 g of magnesium chloride, 10 g of ammonium sulfate, 15 g of agar, 1000 ml of distilled water, pH 7.2.

King B culture medium: 10 g of glycerol, 20 g of peptone, 1.5 g of potassium hydrogenphosphate, 1.5 g of magnesium sulfate, 15 g of agar, pH 7.2.

(11) Urease: +

(12) Oxidase: + (weak)

(13) Catalase: +

(14) Ranges for the growth
- (I) pH: The microorganism grows at pH 4.3 to 7.0. The optimum pH is 5.0 to 6.0.
- (II) Temperature: The microorganism grows at 14° to 32° C. The optimum temperature is 18° to 26° C.

(15) Oxygen demand: Strict aerobic.

(16) O-F (Oxidative-fermentative) test (Hugh.Leifson method): Not reactive

(17) Production of acid and gas from sugars:

|  | Acid Peptone-water | Gas Peptone-water | Utilization (Davis medium) |
|---|---|---|---|
| L-Arabinose | − | − | − |
| D-Xylose | − | − | + |
| D-Glucose | − | − | + |
| D-Mannose | − | − | + |
| D-Fructose | − | − | + |
| D-Galactose | − | − | + |
| Maltose | − | − | − |
| Sucrose | − | − | − |
| Lactose | − | − | − |
| Trehalose | − | − | − |
| D-Sorbitol | − | − | + |
| D-Mannitol | − | − | + |
| Inositol | − | − | + |
| Glycerol | − | − | + |
| Starch | − | − | − |

+: Positive, ±: false positive, −: negative

(18) GC (guanine+cytosine) content in DNA: 68.3±1.5%

When Strain UK-2221 is compared with the species as described in Bergey's Mannual of Determinative Bacteriology, 8th edition, and in International Journal of Systematic Bacteriology, 30, 225–420 (1980) and 32, 146–149 (1982), and in Validation list of the literature, it is reasonable that UK-2221 strain belongs to the genus Pseudomonas, because UK-2221 strain is gram-negative rod, is motile by a single polar flagellum, is strict aerobic, positive to catalase, not reactive in O-F test, the GC (guanine+cytosine) content of DNA is 68.3±1.5%. From the above facts, the present inventors named Strain UK-2221 as Pseudomonas sp. UK-2221.

The above Pseudomonas sp. UK-2221 has been deposited as of August 31, 1984 at IFO, Japan under the accession number of IFO 14366, and this microorganism has also been deposited as of Sept. 7, 1984 at FRI, Japan under the accession number of FERM P-7836 and the deposit has been converted to deposit under the Budapest Treaty and has been stored at FRI under the accession number of FERM BP-637.

The microorganisms of the genera Trigonopsis and Pseudomonas which are used in the present invention are generally liable to vary its characteristics, and can be easily caused to undergo mutation by aritificial mutation means using for example ultraviolet light, X-rays and chemical agents (e.g. nitrosoguanidine, ethylmethanesulfonic acid, etc.). Any of such mutants can also be used in the present invention insofar as they have the converting ability of the present invention.

The "culture broth" as used in the present invention means the product obtained by the cultivation of the microorganism employed in the present invention.

The medium for use in the cultivation of the present invention may optionally be a liquid medium or a solid medium, although the former is more convenient. While the cultural method may optionally be surface culture or shake culture, submerged aerobic culture is advantageous for a large scale production.

In the culture medium, carbon sources which are assimilable to the microorganism used, nitrogen sources which are digestable by the microorganism, inorganic substances, nutritive substances and so forth are added. As the carbon source, glucose, maltose, spent molasses, fats and oils (e.g., soybean oil, olive oil, etc.) and organic acids (e.g., citric acid, succinic acid, gluconic acid, etc.). As the nitrogen source, organic nitrogen compounds and inorganic nitrogen compounds, such as soybean meal, cottonseed meal, corn steep liquor, dried yeast, yeast extract, meat extract, peptone, urea, ammonium sulfate, ammonium nitrate, ammonium chloride and ammonium phosphate, can be utilized. As the inorganic salt, inorganic salts which are normally required for the cultivation of microorganisms, such as sodium chloride, potassium chloride, calcium carbonate, magnesium sulfate, monopotassium phosphate and disodium phosphate, are used solely or in suitable combination.

The medium for use in the cultivation of the microorganism belonging to the genus Trigonopsis may contain D-amino acid (e.g. D-alanine, D-methionine) or D-α-aminoadipic acid.

In the case of liquid culture, any of stationary culture, submerged culture, shake culture, aerated culture, etc. may be conducted, though submerged aerobic culture is particularly preferable for a large scale production.

The cultivation conditions of the microorganism belonging to the genus Trigonopsis vary with the state of the medium, composition of the medium, means of the cultivation. The preferable conditions are as follows: Temperature: about 20° to 45° C., preferably about 24° to 37° C. pH of the medium: about 6 to 9, preferably about 6 to 8. Cultivation time: about 24 to 144 hours, preferably about 24 to 120 hours.

The cultivation conditions of the microorganism belonging to the genus Pseudomonas vary with the state of the medium, composition of the medium, means of the cultivation. The preferable conditions are as follows: Temperature: about 20° to 45° C., preferably about 24° to 37° C. pH of the medium: about 6 to 9, preferably about 6 to 8. Cultivation time: about 24 to 144 hours, preferably about 24 to 120 hours.

The term "processed matter of the culture broth" as used in the present invention means cells or disrupted cells containing the enzyme participating in the process of the present invention, which are obtainable by subjecting the above-mentioned culture broth to any of filtration, centrifugation, ultrasonic distruption, French-press treatment, osmotic shock treatment, freeze-melt treatment, alumina grinding, bacteriolytic enzyme treatment, detergent treatment, organic solvent treatment, etc.

The concentration of the compound (IV) in the reaction of contacting the compound (IV) with the culture broth or processed matter of the culture broth of the microorganism belonging to the genus Trigonopsis is about 0.5 to 20 mg/ml, preferably about 5 to 10 mg/ml. The amount of the cells is about 0.1 to 1 g/ml, preferably about 0.1 to 0.3 g/ml as wet cells, and the amount of the processed matter is calculated from the amount of the wet cells. The pH of the reaction system is adjusted to about 6 to 10, preferably about 7.5 to 8.5. The reaction temperature is about 15° to 40° C., preferably about 15° to 37° C. The reaction time is about 4 to 48 hours, preferably 8 to 16 hours. The reaction may be stationary, shaking, aerobic or agitating, and particularly shaking, aerobic or agitating method is preferable.

In order to recover the objective compound (III) in a good yield, catalase inhibitors may be added to the reaction system. Examples of the catalase inhibitor include inorganic azide (e.g. sodium azide), ascorbic acid, and 3-amino-1,2,3-triazole. To confirm the proceeding or termination of the reaction, it may be carried out by detecting the disappearance of the antimicrobial activity against *Escherichia coli* or by thin layer chromatography or high performance liquid chromatography. After the reaction is completed, the reaction mixture is subjected to centrifugation to remove cells, and the objective compound (III) is isolated and purified from the supernatant.

The present process may be carried out concomitant with the cultivation of the microorganism belonging to the genus Trigonopsis. In that case the compound (IV) is added to the culture medium before the cultivation. The amount of the compound to be added is about 1 to 20 mg/ml, preferably about 2 to 10 mg/ml. The cultivation temperature, pH of the medium and the cultivation time are the same as those of the cultivation of the microorganism.

In the course of the present reaction, the group

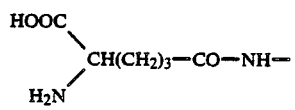

is firstly converted to the group HOOC—CO—(CH$_2$)$_3$—CO—NH—, and the group is immediately converted to the group HOOC—(CH$_2$)$_3$—CO—NH—, namely the compound (III) is obtained.

The concentration of the compound (III) in the reaction of contacting the compound (III) with the culture broth or processed matter of the culture broth of the microorganism belonging to the genus Pseudomonas is about 2 to 20 mg/ml, preferably about 4 to 10 mg/ml. The amount of the cells is about 0.1 to 1 g/ml, preferably about 0.1 to 0.3 g/ml as wet cells, and the amount of the processed matter is calculated from the amount of the wet cells. The pH of the reaction system is adjusted to about 6 to 10, preferably about 6.5 to 7.5. The reaction temperature is about 15° to 40° C., preferably about 15° to 37° C. The reaction time is about 4 to 66 hours, preferably 16 to 54 hours. The reaction may be stationary, shaking, aerobic or agitating, and particularly shaking, aerobic or agitating method is preferable.

The present process may be carried out concomitant with the cultivation of the microorganism belonging to the genus Pseudomonas. In that case the compound (III) is added to the culture medium before the cultivation. The amount of the compound to be added is about 2 to 20 mg/ml, preferably about 4 to 10 mg/ml. The cultivation temperature, pH of the medium and the cultivation time are the same as those of the cultivation of the microorganism.

For the purpose of isolating the compound (IV), (III) or (II) or DCPC from the reaction solution, means generally employed in the isolation of water-soluble acidic substances are utilized in suitable combinations. Thus, adsorption chromatography with various adsorbent carriers, ion exchange chromatography with ion exchange resins, gel filtration, reverse-phase liquid chromatography, or such means as concentration under reduced pressure and lyophilization are employed singly, in combination in arbitrary or repeatedly. As the adsorbent supports, there are used activated carbon, adsorptive resins, anion-exchange resins, powdery cellulose, etc., or supports having the molecular sieve effect and the like are also utilized. As the eluting solvent, which varies with the kind of the supports, there are used, for example, water-soluble organic solvents, water-containing solutions of acetone, methanol, propanol, butanol, isopropanol, isobutanol, etc., or acids, alkalis, buffers or aqueous solutions of inorganic or organic salts.

Referring in more detail to their examples, the reaction solution after the conclusion of the reaction is adjusted to a pH in the neighborhood of about 6 to 7, and because the substance in question is an acid substance, the reaction solution is passed through a Cl$^-$ or AcO$^-$ type of a support, such as anion exchange resins [e.g., Amberlite IRA-68, 402, 410 (Rohm & Haas Co., U.S.A.), Dowex-1 (Dow Chemical Co., U.S.A.), Diaion SA-21C (Mitsubishi Chemical Industries, Ltd., Japan), etc.] to adsorb the antibiotic. As the eluting solution for the substance in question thus adsorbed, there is used an aqueous sodium chloride solution or buffer to elute the active substance. For desalting the eluate, the eluate is made neutral to weakly acid and subjected to activated carbon (Takeda Chemical Industries, Ltd., Japan) chromatography, followed by elution with water-containing alcohols, etc.

Subsequently, the eluate containing active substance is concentrated under reduced pressure at a low temperature, and the concentrate is passed through a Cl$^-$ type of a resin of DEAE or QAE Sephadex (Pharmacia Co., Sweden) to adsorb the antibiotic. The adsorbed antibiotic is eluted and fractionated with dilute aqueous sodium chloride solution. The effective fractions are detected by means of high performance liquid chromatography, and the eluates are collected and subjected to activated carbon chromatography, followed by desalting. The eluate is concentrated, and the concentrate is lyophilized. Acetone is added to the lyophilized powder, and the resulting precipitate is recovered by filtration.

The thus-obtained salt of the compound can be converted into other salts by use of per se known means. For example, the obtained salt is dissolved in water, and the solution is adjusted to a pH of about 2 to 3 under cooling with dilute hydrochloric acid. The aqueous solution is immediately adjusted to a pH of about 7 to 8 with a dilute aqueous alkali solution, such as aqueous solutions containing sodium hydroxide, calcium hydroxide, methylamine, tetrabutylammonium hydroxide, etc., to produce the desired salt, and the said aqueous solution is subjected to chromatography on activated carbon. After washing the inorganic or organic salt with water, the salt of the objective compound is eluted.

The sodium salt of 7-FA-DCPC [compound (IV)] obtained in Example 1 to be described below shows the physicochemical properties as mentioned in the following.

(1) Appearance:
   White powder
(2) Specific rotation:

$$[\alpha]_D^{25} + 146.5° \pm 30° \ (c=0.51, \text{water})$$

(3) Molecular weight:
   438 (in accordance with the SIMS method)
(4) Elemental analysis (%), for $C_{15}H_{19}N_4O_8SNa \cdot H_2O$:

| | Found | Calcd. |
|---|---|---|
| C | 39.65 ± 2.0 | 39.48 |
| H | 4.64 ± 0.5 | 4.64 |
| N | 12.20 ± 1.0 | 12.28 |
| O | | 31.55 |
| S | 7.28 ± 1.0 | 7.02 |
| Na | 5.2 ± 1.0 | 5.04 |

(5) Ultraviolet absorption (UV) spectrum:

$\lambda_{max}^{H_2O}(E_1 \, cm^{1\%}) 258 \pm 2$ nm $(209 \pm 50)$

Refer to FIG. 1.
(6) Infrared absorption (IR) spectrum (KBr method): Principal peaks
3430, 3240, 3020, 1770, 1680, 1610, 1520, 1410, 1375, 1300, 1220, 1145, 1070, 1040, 1000, 800, 710, 540 cm$^{-1}$ Refer to FIG. 2.
(7) $^{13}$C Nuclear magnetic resonance (NMR) spectrum (100 MHz, in D$_2$O):
δ 179.65(s), 177.22(s), 171.43(s), 166.30(d), 162.01(s), 132.76(s), 122.50(s), 79.47(s), 66.03(d), 63.75(t), 57.33(d), 37.28(t), 32.70(t), 28.22(t), 23.40(t) ppm (s stands for singlet; d doublet and t triplet).
(8) High performance liquid chromatography (HPLC) (Waters Associates, U.S.A.):
Column: YMC-Pak A-312 (Yamamura Chemical Laboratories, Japan). Mobile phase: 2% methanol-0.01M phosphate solution (pH 3.0). Flow rate: 2 ml/min, Rt=2.3 minutes.
(9) Color reactions:
Positive: Ninhydrin reaction
Negative: Ehrlich reaction, Graig-Leaback reaction, Sakaguchi reaction
(10) Solubility:
Readily soluble in water
Soluble in methanol
Sparingly soluble in diethyl ether and ethyl acetate.
On the basis of the above physico-chemical properties, it is thought that the compound obtained by subjecting TAN-547 A, B or C to a hydrolysis reaction is 7-FA-DCPC as represented by the above formula (IV).

The sodium salt of 7-FA-DCPC [compound (IV)] obtained in Example 9 to be described below shows the physico-chemical properties as mentioned in the following.
(1) Appearance:
White powder
(2) Specific rotation:

$[\alpha]_D^{25} + 150° \pm 30°$ (c=0.55, water)

(3) Molecular weight:
438 (in accordance with the SIMS method)
(4) Elemental analysis (%), for C$_{15}$H$_{19}$N$_4$O$_8$SNa.H$_2$O:

| | Found | Calcd. |
|---|---|---|
| C | 39.8 ± 2.0 | 39.48 |
| H | 4.9 ± 0.5 | 4.64 |
| N | 12.3 ± 1.0 | 12.28 |
| O | | 31.55 |
| S | 6.9 ± 1.0 | 7.02 |
| Na | 5.4 ± 1.0 | 5.04 |

(5) Ultraviolet absorption (UV) spectrum:

$\lambda_{max}^{H_2O}(E_1 \, cm^{1\%}) 258 \pm 2$ nm $(200 \pm 50)$

Refer to FIG. 4.
(6) Infrared absorption (IR) spectrum (KBr method): Principal peaks
3430, 3240, 3020, 1770, 1680, 1610, 1520, 1410, 1375, 1300, 1220, 1145, 1070, 1040, 1000, 800, 710, 540 cm$^{-1}$
Refer to FIG. 5.
(7) $^{13}$C Nuclear magnetic resonance (NMR) spectrum (100 MHz, in D$_2$O):
δ 179.7 (s), 177.2 (s), 171.4 (s), 166.3 (d), 162.0 (s), 132.7 (s), 122.5 (s), 79.5 (s), 66.0 (d), 63.8 (t), 57.3 (d), 37.3 (t), 32.7 (t), 28.2 (t), 23.4 (t) ppm (s stands for singlet; d doublet and t triplet)
(8) High performance liquid chromatography (HPLC) (Waters Associates, U.S.A.):
Column: YMC-Pak A-312 (Yamamura Chemical Laboratories, Japan). Mobile phase: 2% methanol-0.01M phosphate solution (pH 3.0). Flow rate: 2 ml/min, Rt=2.3 minutes.
(9) Color reactions:
Positive: Ninhydrin reaction
Negative: Ehrlich reaction, Graig-Leaback reaction, Sakaguchi reaction
(10) Solubility:
Readily soluble in water
Soluble in methanol
Sparingly soluble in diethyl ether and ethyl acetate.
On the basis of the above physico-chemical properties, it is thought that the compound obtained by subjecting TAN-592 A, B or C or TAN-591 A, B or C to a hydrolysis reaction is 7-FA-DCPC as represented by the above formula (IV).

Sodium salt of DCPC obtained in Examples 5 and 17 to be described below is identical with the authentic sample of DCPC by the IR (FIGS. 3 and 6), UV, $^{13}$C NMR and mass spectra, elemental analysis, Rt value on HPLC and an antimicrobial spectrum.

DCPC is a known compound and is useful, for example, as an intermediate for the production of cephem antibiotics.

The physico-chemical properties of the disodium salt of the compound (III) obtained in Example 21 mentioned hereinafter are as follows.
(1) Appearance: white powder
(2) Molecular weight: molecular ion peak m/z 432 (M+H)$^+$ by SIMS method (3) Elemental analysis: (40° C., dried for 8 hours under reduced pressure)

| | Found | Calcd. |
|---|---|---|
| C | 38.06 | 38.19 |
| H | 3.81 | 3.66 |
| N | 9.97 | 9.54 |
| O | | 30.88 |
| S | 7.68 | 7.28 |
| Na | | 10.44 |

(4) Molecular formula: C$_{14}$H$_{15}$N$_3$O$_8$SNa$_2$.0.5H$_2$O
(5) UV spectrum (in water):

$\lambda_{max}^{H_2O} 259$ nm $(E_1^{1\%}{}_{cm}=224)$ (6) IR spectrum (KBr): main wave number (cm$^{-1}$)
3400, 3230, 3010, 1775, 1700, 1690, 1610, 1580, 1410, 1305, 1240, 1150, 1065, 1045, 1000, 850, 800, 710, 515

Refer to FIG. 7.

(7) $^1$H NMR spectrum: 100 MHz, in $D_2O$, δ ppm J(Hz) 1.75-2.15, 2H, m, 2.15-2.55, 4H, m, 3.38, 1H, d, J=18, 3.70, 1H, d, J=18, 4.27, 2H, s, 5.39, 1H, s, 8.21, 1H, s.

(8) HPLC: Waters Assoc., U.S.A., Model 6000A/660/440

Column: YMC-Pack A-312 Mobile phase: 0.01M phosphate buffer (pH 6.3), 2 ml/min. Detection: 254 nm Rt=3.1 min.

The physico-chemical properties of the compound (II) obtained in Example 22 mentioned hereinafter are as follows:

(1) Appearance: white powder
(2) Molecular weight: molecular ion peak, m/z 296 (M+Na)$^+$ by SIMS Method
(3) Molecular formula: $C_9H_{11}N_3O_5S$ (273)
(4) UV spectrum:

$\lambda_{max}^{H_2O}$ 259 nm ($E_1^{1\%}{}_{cn}$=365)

(5) CD spectrum:

$[\theta]_{229}^{H_2O}$ −33300±5000 and $[\theta]_{260}^{H_2O}$ +32400±5000

(6) IR spectrum: Main absorption (cm$^{-1}$)
3400, 2980, 1760, 1680, 1600, 1510, 1410, 1380, 1290, 1240, 1180, 1140, 1070, 1040, 1000, 860, 790, 700, 500
Refer to FIG. 8.

(7) $^1$H NMR spectrum: 400 MHz, in $D_2O$,

δ ppm J(Hz) 3.43, 1H, d, J=17.6, 3.65, 1H, d, J=17.6, 4.21, 1H, d, J=12.9, 4.25, 1H, d, J=12.9, 5.19, 1H, s, 8.17, 1H, s.

(8) HPLC: Model 638-50 (Hitachi Co., Japan) Column: YMC-Pack A-312

Mobile phase: 0.01M phosphate buffer (pH 6.3), 2 ml/min. Detection: 254 nm Rt=3.0 min.

Reference is to be made below to biological properties of 7-FA-DCPC. The sodium salt of 7-FA-DCPC demonstrates the antibacterial spectrum as shown in Table 1. As is obvious from this table, Antibiotic 7-FA-DCPC exhibits antibacterial activity against gram-positive and gram-negative bacteria.

TABLE 1

Antibacterial spectrum of Antibiotic 7-FA-DCPC sodium salt.

| Test organism | Minimal inhibitory concentration (μg/ml) |
|---|---|
| Escherichia coli NIHJ JC-2 | 50 |
| Salmonella typhimurium IFO 12529 | 25 |
| Klebsiella pneumoniae IFO 3317 | 50 |
| Proteus vulgaris IFO 3988 | 25 |
| Proteus mirabilis ATCC 21100 | 12.5 |
| Serratia marcescens IFO 12648 | 25 |
| Alcaligenes faecalis IFO 13111 | 12.5 |
| Pseudomonas aeruginosa IFO 3080 | 100 |
| Staphylococcus aureus FDA 209P | 100 |
| Bacillus subtilis NIHJ PCI219 | 100 |
| Bacillus megaterium IFO 12108 | 100 |

Note:
Culture medium: Nutrient agar (pH 7.0) concentration of microorganisms inoculated: 10$^6$ CFU (colony forming unit)/ml.

In addition, the sodium salt of 7-FA-DCPC is stable to various β-lactamases. The stabilities of 7-FA-DCPC and DCPC to β-lactamases are shown in Table 2.

TABLE 2

| Stability to β-lactamases | | | |
|---|---|---|---|
| | Diameter of growth inhibition zone (mm) (by the disc method) | | |
| Enzyme | 7-FA-DCPC | DCPC | CMC (Note 1) |
| Non-added control | 23 | 30 | 30 |
| Penicillinase (Note 2) | 23 | 30 | 30 |
| Cephalosporinase (Note 3) | 23 | <8 | <8 |

Note: Used concentration of the compound: 100 g/ml Employed strain: *Escherichia coli* PG8 Culture medium; Nutrient agar medium (pH 7.0) containing diaminopimelic acid (20 mg/l)
(Note 1) CMC: Cephamycin C
(Note 2) Penicillinase derived from *Bacillus cereus* (produced by Calbio Chemical. U.S.A.)0.048 unit/ml.
(Note 3) Cephalosprinase is derived from *Enterobacter cloacae*, 0.025 unit/ml.

Furthermore, the therapeutic effect of sodium salt of 7-FA-DCPC to infectious disease in mice is shown in Table 3.

TABLE 3

| Infection organism | Route of administration | ED$_{50}$ (mg/kg) |
|---|---|---|
| *Escherichia coli* | subcutaneous | ca. 100 |
| O-111* | subcutaneous | 59.5 |

*Intraperitoneal infection

When sodium salt of 7-FA-DCPC was administered subcutaneously in the dose of 1 g/kg to mice, no death was observed, and consequently, 7-FA-DCPC is considered to have low toxicity.

As is evident from these data, the compound (IV) exhibits antimicrobial activity against gram-positive and negative bacteria, and is an antibiotic with low toxicity to mammals, etc. And the compound (IV) wherein R$^1$ is formylamino is stable to β-lactamase producing strains. Therefore, the compound (IV) can be used in the treatment of infectious disease caused by bacteria in mammals (e.g., mouse, rat, rabbit, dog, human being, etc.).

In order to use the compound (IV) for example as a therapeutic agent against infectious disease caused by bacteria, the compound (IV) is administered, for example as an injection by a route other than oral route, to the above mammals subcutaneously or intramuscularly in the dose of about 2 to 100 mg/kg/day, preferably about 10 to 50 mg/kg/day. As preparations for oral administration, the compound (IV) is formulated into capsules, which are administered in the dose of about 10 to 200 mg/kg/day as the compound (IV), preferably about 20 to 100 mg/kg/day.

In addition, the compound (IV) can be used as a bactericide. The compound (IV), for example, is made into a liquid preparation having the compound (IV) in concentration of about 0.02 to 0.2 w/v % dissolved in distilled water, and an ointment containing about 0.5 to 50 mg, preferably about 2 to 20 mg of the compound (IV) per gram of the preparation, and they can be applied for sterilization and disinfection of hands, feet, eyes, ears, etc. of the above mammals by coating them on these parts of the body.

The compound (IV) is also a highly valuable compound as an intermediate for the synthesis of new drugs.

The hydrolysis of the present invention involves selective cleavage of the ester linkage at the 3-position, resulting in increased yields of the object compound (IV), and the process of the present invention constitutes an advantageous process in the industrial production thereof.

Since the starting compound (V) in the process of the present invention can be produced in large amounts in a shortened period of time by the cultivation of bacteria, furthermore, the said fermentation method followed by the process of the present invention can permit the object compound (IV) to be produced in large quantities and in improved yields in a reduced length of time, thus providing a process favored for the industrial production of the compound (IV).

Compound (III) is useful as an intermediate for the production of a cephem antibiotic, for example the present compound (II).

Reference is to be made below to biological properties of the compound (II). The sodium salt of the compound (II) demonstrates the antibacterial spectrum as shown in Table 4. As is obvious from this table, the compound (II) exhibits antibacterial activity against gram-negative bacteria.

TABLE 4

Antibacterial spectrum of the compound (II) sodium salt.

| Test microorganism | Diameter of growth inhibition zone (mm) (see note) |
|---|---|
| *Escherichia coli* CP 13 | 11 |
| *Pseudomonas aeruginosa* C141 | 19 |
| *Staphylococcus aureus* FDA 209P | <8 |

Note:
Culture medium: Nutrient agar medium (pH 7.0) containing diaminopimeric acid (20 mg/l)
Concentration of the compound (II): 1000 μg/ml.

In addition, the sodium salt of the compound (II) is stable to various $\beta$-lactamases. The stabilities to $\beta$-lactamases of the compound (II) and DCPC are shown in Table 5.

TABLE 5

Stability to $\beta$-lactamases

| Enzyme | Diameter of growth inhibition zone (mm) (by the disc method) | | |
|---|---|---|---|
| | Compound (II) | DCPC (Note 1) | CMC (Note 2) |
| Non-added control | 19 | 30 | 27.5 |
| Penicillinase (Note 2) | 19 | 30 | 27.5 |
| Cephalosporinase (Note 3) | 19 | <8 | <8 |

Note:
Concentration of the compound (II) 1000 μg/ml
Concentration of the other compounds: 100 μg/ml
Strain used: Pseudomonas aeruginosa C141
Culture medium: Nutrient agar medium (pH 7.0) containing diaminopimeric acid (20 mg/l)
(Note 1) DCPC: deacetylcephalosporin C
(Note 2) CMC: cephamycin C
(Note 3) Penicillinase (Calbio Chemical, U.S.A.) derived from *Bacillus cereus*, 0.048 unit/ml.
(Note 4) The enzyme is derived from *Enterobacter cloacae*, 0.025 unit/ml.

When sodium salt of the compound (II) was administered subcutaneously in the dose of 1 g/kg to mice, no death was observed, and consequently, the compound (II) is considered to have low toxicity.

As is evident from these data, the compound (II) exhibits antimicrobial activity against negative bacteria, and is an antibiotic with low toxicity. Therefore, the compound (II) can be used in the treatment of infectious disease caused by bacteria in mammals (e.g., mouse, cattle, horse, dog, human being, etc.) or poultries (e.g. a domestic fowl, duck).

In order to use the compound (II) for example as a therapeutic agent against infectious disease caused by bacteria, the compound (II) is administered, for example as an injection by a route other than oral route, to the above mammals subcutaneously or intramuscularly in the dose of about 5 to 200 mg/kg/day, preferably about 20 to 200 mg/kg/day. As preparations for oral administration, the compound (II) is formulated into capsules, which are administered in the dose of about 20 to 400 mg/kg/day as the compound (II), preferably about 40 to 200 mg/kg/day.

In addition, the compound (II) can be used as a bactericide. The compound (II), for example, is made into a liquid preparation having the compound (II) in concentration of about 0.05 to 0.4 w/v % dissolved in distilled water, and an ointment containing about 1 to 100 mg, preferably about 4 to 50 mg of the compound (II) per gram of the preparation, and they can be applied for sterilization and disinfection of hands, feet, eyes, ears, etc. of the above mammals by coating them on these parts of the body.

The compound (II) is also a highly valuable compound as an intermediate for the synthesis of cephem compounds.

It is known from the comparison between cephalosporin C and deacetylcephalosporin C that a cephalosporin derivative which is acetylated at 3-position is unstable. However, the present compound (II), which has a group —$CH_2OH$ at 3-position, is remarkably more stable in aqueous solution than a cephem compound which is acetylated (which has a group —$CH_2OCOCH_3$ at 3-position). This fact shows that the present compound (II) is easily employed as an intermediate in a reaction for the production of cephem compounds.

Figure 1:
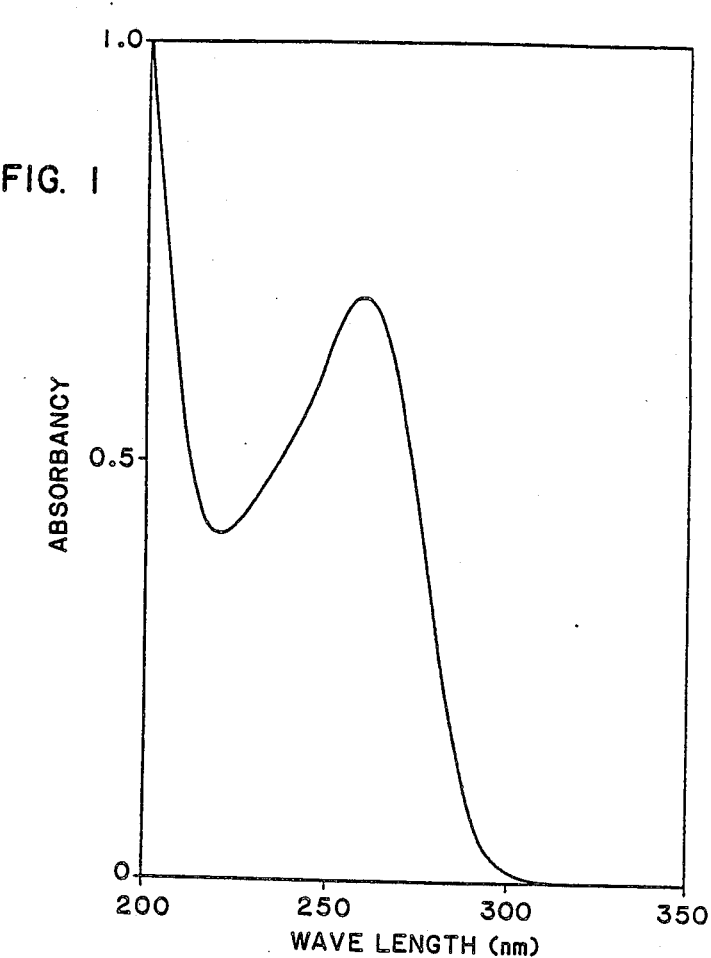
FIGS. 1 and 4 show the ultraviolet absorption spectra of the compound (IV) obtained in Examples 1 and 9.
Figure 2:
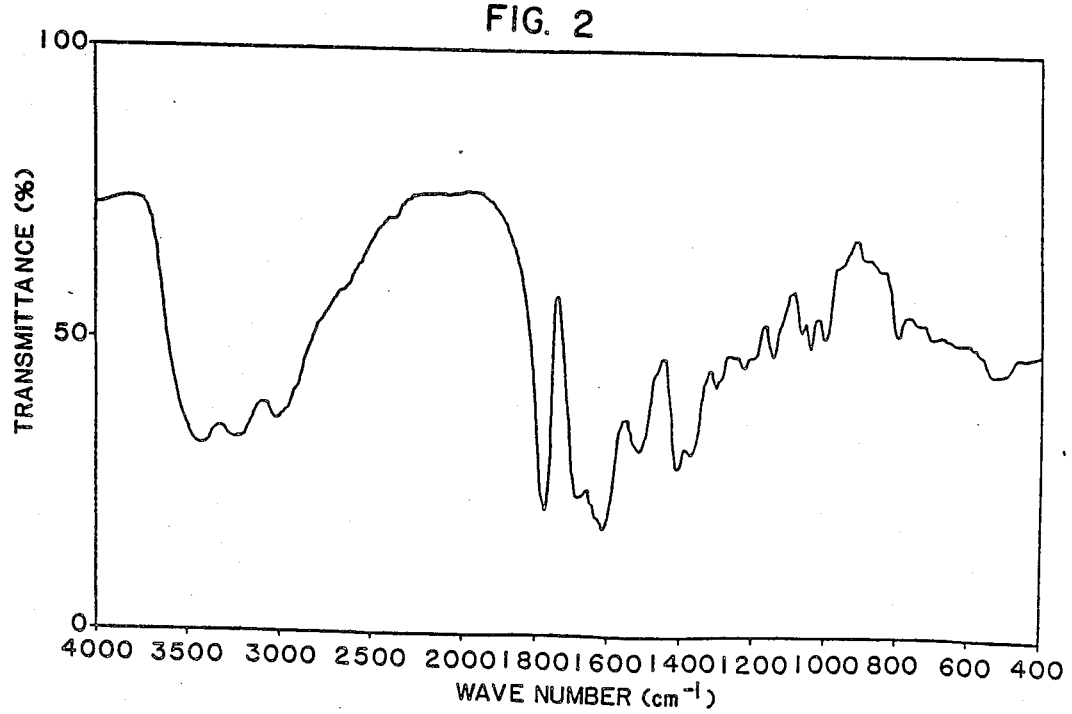
FIGS. 2, 3, 5, 6, 7 and 8 show the infrared absorption spectra of the compound (IV) obtained in Example 1, of the compound (IV) obtained in Example 9, of DCPC obtained in Example 5, of DCPC obtained in Example 17, of the compound (III) obtained in Example 21 and of the compound (II) obtained in Example 22.

The reference Examples and Examples are described in the following to illustrate the present invention more in detail. The term % in the culture medium means a weight/volume %, unless otherwise noted.

REFERENCE EXAMPLE 1

(1) *Lysobacter lactamgenus* YK-90 (IFO 14288, FERM BP-575) grown on a nutrient agar slant was used to inoculate three 200-ml Erlenmeyer flasks each containing 40 ml of a culture medium of an aqueous solution (pH 7) composed of 2% of glucose, 3% of soluble starch, 1% of raw soybean flour, 1% of corn steep liquor, 0.5% of Polypepton (produced by Daigo Nutritive Chemicals, Ltd., Japan) and 0.3% of sodium chloride and 0.5% of precipitating calcium carbonate admixed, and shake culture was carried out on a rotary shaker at 24° C. for 48 hours to obtain seed cultures.

Then, 4000 ml of a culture medium consisting of an aqueous solution (pH 6.5) containing 3% of dextrin, 1.5% of raw soybean flour, 1.5% of corn gluten meal, 0.2% of Polypepton and 0.1% of sodium thiosulfate and 0.5% of precipitating calcium carbonate admixed were distributed in 40-ml portions into 200-ml Erlenmeyer flasks, which were then sterilized at 120° C. for 20 minutes. A 1-ml portion of the seed culture was transferred to each of these 200-ml Erlenmeyer flasks containing the said culture medium, and incubated on a rotary shaker at 24° C. for 72 hours under the conditions of 200 r.p.m.

The culture broth (20 l) obtained by the above procedure was adjusted to pH 3.5 with 7% oxalic acid, admixed with Hyflo-Super Cel (Johns Manville Product, U.S.A.) and filtered to obtain a filtrate (16 l). The filtrate was adjusted to pH 6.8, and passed through a column packed with activated carbon (1 l). The column was washed with water (3 l), and Antibiotic TAN-547 was eluted with 8% isobutanol-N/200 hydrochloric acid (8 l). The eluate was concentrated to 1.8 l, and the concentrate was passed through a column of Amberlite CG-50 ($H^+$ type, 1.4 l) (produced by Rohm & Haas Co., U.S.A.). The column was washed with water (4.5 l), and the elution was conducted with N/100 hydrochloric acid (9 l) by fractionation. The active fractions were collected and concentrated, and the concentrate was adjusted to pH 7.3 and passed through a column packed with Diaion HP-20 (50 to 100 mesh, 0.5 l) (produced by Mitsubishi Chemical Industries, Ltd., Japan). After the column was washed with 0.01M phosphate buffer (pH 7.3, 1.5 l), elution was conducted with 0.01M phosphate buffer (pH 3.5, 5 l) by fractionation. The active fractions were collected, and the eluate was adjusted to pH 7.2 and passed through a column packed with activated carbon (100 ml). The column was washed with water (300 ml), and elution was carried out with 8% isobutanol-N/200 hydrochloric acid (600 ml). The eluate was concentrated, and the concentrate was passed through a column packed with CM-Sephadex C 25 ($Na^+$ type, 200 ml) (produced by Pharmacia Fine Chemicals Co., Sweden), followed by elution with 0.02M aqueous sodium chloride solution (6 l). Individual fractions were subjected to analysis by HPLC, and the fractions respectively containing TAN-547 A, B and C as the principal component, were collected.

The fraction containing TAN-547 A as a principal component was adjusted to pH 7.2, and passed through a column packed with activated carbon (10 ml), and after the column was washed with water (30 ml), elution was carried out with 8% isobutanol-N/200 hydrochloric acid (70 ml). The eluate was concentrated, and the concentrate was lyophilized to give a crude powder (61 mg) of TAN-547 A.dihydrochloride.

By conducting the same procedure with the fractions containing TAN-547 B and C as a principal component, respectively, there were obtained a crude powder (144 mg) of TAN-547 B.dihydrochloride and a crude powder (226 mg) of TAN-547 C.dihydrochloride.

The crude powder (61 mg) of TAN-547 A.dihydrochloride was subjected to preparative HPLC for separation with YMC-GEL ODS I-15 (produced by Yamamura Chemical Laboratories, Japan) used as a support, and elution fractionation was carried out with 0.02M phosphate buffer (pH 3.0). The individual fractions were subjected to analysis by HPLC, and the fractions showing a single peak were collected. The active fraction was adjusted to pH 7.5 with 1N NaOH, readjusted to pH 3.0 with 1N HCl, and passed through a column packed with activated carbon (5 ml). After the column was washed with water (25 ml), elution was conducted with 8% aqueous isobutanol (25 ml). The eluate was concentrated and lyophilized to give a white powder (40 mg) of TAN-547 A.dihydrochloride.

Crude powders of TAN-547 B and C.dihydrochlorides were also subjected to preparative HPLC for separation in the same manner to yield a white powder (96 mg) of TAN-547 B.dihydrochloride and a white powder (112 mg) of TAN-547 C.dihydrochloride.

(2) *Lysobacter lactamgenus* YK-90 (IFO 14288, FERM BP-575) grown on a nitrient agar slant was used to inoculate two 2-l Sakaguchi flasks each containing 500 ml of a culture medium consisting of an aqueous solution (pH 7.0) having the composition of 2% of glucose, 3% of soluble starch, 1% of raw soybean flour, 1% of corn steep liquor, 0.5% of Polypepton and 0.3% of sodium chloride admixed with 0.5% of precipitating calcium carbonate, and incubated on a reciprocal shaker at 24° C. for 48 hours. The total volume of the resulting culture broth was transferred to a tank of a 200-l capacity containing 120 l of the above-described culture medium being admixed with 0.05% of an antifoam, Actcol (produced by Takeda Chemical Industries, Ltd., Japan), and incubation was carried out at 24° C. for 48 hours with aeration at the rate of 120 l/min. and agitation at 150 r.p.m. The total volume of the resulting culture broth was transferred to a tank of a 6000-l capacity containing 4000 l of a culture medium consisting of an aqueous solution (pH 6.5) having the composition of 3% of dextrin, 1.5% of raw soybean flour, 1.5% of corn gluten meal, 0.2% of Polypepton and 0.1% of sodium thiosulfate admixed with 0.5% of precipitating calcium carbonate and 0.05% of Actcol, and incubation was carried out at 24° C. for 66 hours with aeration at the rate of 4000 l/min and agitation at 120 r.p.m.

The culture (3900 l) obtained by the above procedure was adjusted to pH 6.1 with 2N hydrochloric acid, admixed with Hyflo-Super Cel, filtered and wahsed with water to give a filtrate (4370 l). The filtrate was adjusted to pH 7.0 and passed through a column packed with Dowex-50W $Na^+$ type, 50 to 100 mesh, 120 l). The column was washed with water (360 l), and elution was carried out with 2M aqueous sodium chloride solution (1800 l). The eluate was passed through a column of activated carbon (60 l), and after the column was washed with water (180 l), elution was carried out with 8% isobutanol-N/200 hydrochloric acid (420 l). The eluate was concentrated to 40 l, and the concentrate was adjusted to pH 7.3 and passed through a column packed with Diaion HP-20 (40 l). The column was washed with 0.01M phosphate buffer (pH 7.3, 80 l), and elution was carried out with 0.01M phosphate buffer (pH 3.5, 400 l).

The eluate was passed through a column of activated carbon (10 l), and after the column was washed with water (30 l), elution was carried out with 8% isobutanol-N/200 hydrochloric acid (70 l). The eluate was concentrated to 2 l, and the concentrate was adjusted to pH 7.3 and passed through a column packed with Diaion HP-20 (50 to 100 mesh, 4 l). The column was washed with 0.01M phosphate buffer (pH 7.3, 12 l), elution was carried out with 0.01M phosphate buffer (pH 3.5, 40 l). Individual fractions were subjected to analysis by HPLC and separated into two groups, fractions containing TAN-547 A, B and C as a principal component and fractions containing TAN-547 D, E and F as a principal component. The fractions containing TAN-547 D, E and F were collected and passed through a column of activated carbon (300 ml), and after the column was washed with water, elution was carried out 8% isobutanol-N/200 hydrochloric acid (2100 ml). After the eluate was concentrated, the concentrate was passed through a column packed with CM-Sephadex C 25 ($Na^+$ type, 300 ml), and elution was carried out with 0.02M aqueous sodium chloride solution (12 l). Individual fractions were subjected to analysis by HPLC, and fractions containing TAN-547 D, E and F as a principal component, respectively, were collected.

The fractions containing TAN-547 F as a principal component were collected and passed through a column of activated carbon (50 ml), and the column was washed with water (150 ml), followed by elution with 8% isobutanol-N/200 hydrochloric acid (350 ml). The eluate was concentrated and the concentrate was lyophilized to give a crude powder (1.0 g) of TAN-547 F. The same procedure were conducted with the fractions containing TAN-547 D and E as a principal component, respectively, and there were obtained a crude powder (0.3 g) of TAN-547 D and a crude powder (0.6 g) of TAN-547 E.

The crude powder (1.0 g) of TAN-547 F was subjected to preparative HPLC for separation using YMC-GEL ODS 30/60 (produced by Yamamura Chemical Research Institute of Japan) as a support, and elution fractionation was carried out with 2% methanol-0.02M phosphate buffer (pH 3.0). Individual fractions were subjected to analysis by HPLC, and fractions containing TAN-547 F as a principal component were collected, adjusted to pH 7.1 and passed through a column of activated carbon (20 ml). After the column was washed with water (60 ml), elution was carried out with 8% isobutanol-N/200 hydrochloric acid (140 ml), and the eluate was concentrated. The concentrate was subjected to preparative HPLC for separation using TSK-GEL, LS-410 (produced by Toyo Soda Manufacturing Co. Ltd., Japan) as a support, and elution fractionation was carried out with 1% methanol-0.01M phosphate buffer (pH 3.0). Individual fractions were subjected to analysis by HPLC and fractions showing a single peak were collected. The effective fractions were adjusted to pH 7.0 with 1N NaOH, readjusted to pH 3.0 with 1N HCl and passed through a column packed with activated carbon (10 ml), and after the column was washed with water (50 ml), elution was carried out with 8% aqueous isobutanol solution. The eluate was concentrated, and the concentrate was lyophilized to give a white powder (69 mg) of TAN-547 F dihydrochloride. The crude powders of TAN-547 D and E were also subjected to preparative HPLC for separation in the same manner, and there were obtained a white powder (30 mg) of TAN-547 D monohydrochloride and a white powder (63 mg) of TAN-547 E dihydrochloride.

The physico-chemical properties of Antibiotic TAN-547.dihydrochloride obtained in the above are shown below.

(i) TAN-547A.dihydrochloride:
(1) Appearance: White powder
(2) Specific rotation:

$[\alpha]_D^{25} +71.8° \pm 20°$ (c=0.50, in water)

(3) Molecular weight: SIMS method, $(M+H)^+ 688$
(4) Molecular formula: $C_{26}H_{41}N_9O_{11}S \cdot 2HCl \cdot (3H_2O)$
(5) Elemental analysis(%):

| Found*[1] | Calcd.*[2] |
|---|---|
| C, 38.29 ± 2.0 | C, 38.33 |
| H, 6.48 ± 1.0 | H, 6.06 |
| N, 15.11 ± 1.5 | N, 15.47 |
|  | O, 27.49 |
| S, 4.12 ± 1.0 | S, 3.94 |

-continued

| Found*[1] | Calcd.*[2] |
|---|---|
| Cl, 8.71 ± 1.5 | Cl, 8.70 |

*[1]The sample was dried over diphosphorus pentoxide for 15 hours at room temperature under reduced pressure.
*[2]The value is calculated as the sample contains 3 moles of water.

(6) Ultraviolet absorption (UV) spectrum:

$\lambda_{max}^{H_2O} 260 \pm 2$ nm ($E_1^{1\%}{}_{cm} = 117 \pm 20$)

(7) Circular dichroism (CD) spectrum:

$[\theta]_{228 \pm 2}^{H_2O} -30900 \pm 5000$ and $[\theta]_{260 \pm 2}^{H_2O} +29500 \pm 5000$ (−: negative (−) Cotton effect; +: positive (+) Cotton effect)

(8) Infrared absorption (IR) spectrum: Main wave number (cm$^{-1}$) in KBr tablet:
3420, 3250, 3080, 3000, 1775, 1730, 1670, 1510, 1450, 1400, 1260, 1165, 1060, 980, 860, 510.

(9) Nuclear magnetic resonance ($^{13}$C-NMR) spectrum: in D$_2$O, signals at 100 MHz are shown below (δ ppm).
179.84(s), 177.42(s), 176.05(s), 173.75(s), 171.12(s), 166.40(d), 162.16(s), 159.62(s), 134.86(s), 117.40(s), 79.64(s), 72.66(d), 67.16(t), 65.94(d), 57.34(d), 56.31(d), 52.03(d), 43.59(t), 41.23(t), 37.36(t), 32.80(t), 28.98(t), 28.60(t), 27.50(t), 23.50(t), 19.75(q).

(s: singlet, d: doublet, t: triplet, q: quartet)

(10) Amino acid analysis: in 5.5N-HCl, 110° C., the sample was hydrolized for 15 hours.
Alanine; 0.86 mole α-aminoadipic acid; 0.94 mole
(11) Thin layer chromatography (TLC): Spot film cellulose (Tokyo Chemical Industries, Ltd., Japan)
Solvent system, acetonitrile: 3% ammonium sulfate (1:1), Rf=0.52
(12) High performance liquid chromatography (HPLC): column, YMC pack A312 (Yamamura Chemical Laboratories, Japan), mobile phase, 2% methanol/0.01M phosphate buffer (pH 3.0), 2 ml/min. Rt=5.8 (min)

The following properties are in common among the components A, B and C (dihydrochloride).
(13) Solubility:
Easily soluble: water, aqueous acetone, aqueous alcohol. Sparingly soluble: dimethylsulfoxide, methanol, acetone, ethyl acetate.
(14) Color reaction:
Positive: ninhydrine, Greig-Leaback, Sakaguchi reactions.
Negative: Ehrlich, Barton reactions, potassium permanganate.
(15) Stability:
Unstable in acidic and basic aqueous solution, slightly unstable in neutral aqueous solution
(16) Property of the substance:
Amphoteric substance (dihydrochloride is neutral)
(ii) TAN-547B.dihydrochloride
(1) Appearance: White powder
(2) Specific rotation:

$[\alpha]_D^{25} +54.8° \pm 15°$ (c=0.56, in water)

(3) Molecular weight: SIMS method, $(M+H)^+ 759$ (4) Molecular formula: $C_{29}H_{46}N_{10}O_{12}S \cdot 2HCl \cdot (3H_2O)$
(5) Elemental analysis (%):

| Found*1 | Calcd.*2 |
|---|---|
| C, 39.02 ± 2.0 | C, 39.32 |
| H, 6.51 ± 1.0 | H, 6.14 |
| N, 15.46 ± 1.5 | N, 15.81 |
|  | O, 27.09 |
| S, 3.50 ± 1.0 | S, 3.62 |
| Cl, 8.27 ± 1.5 | Cl, 8.01 |

*1, *2 the same conditions as those of A.

Figure 3:
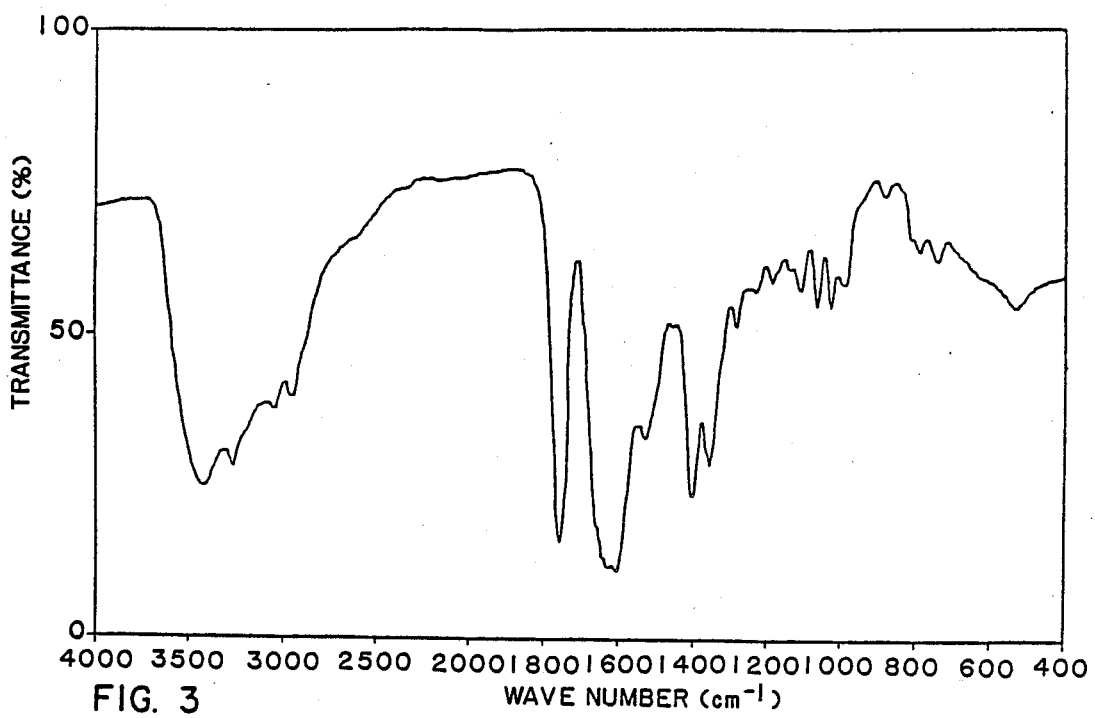
Figure 4:
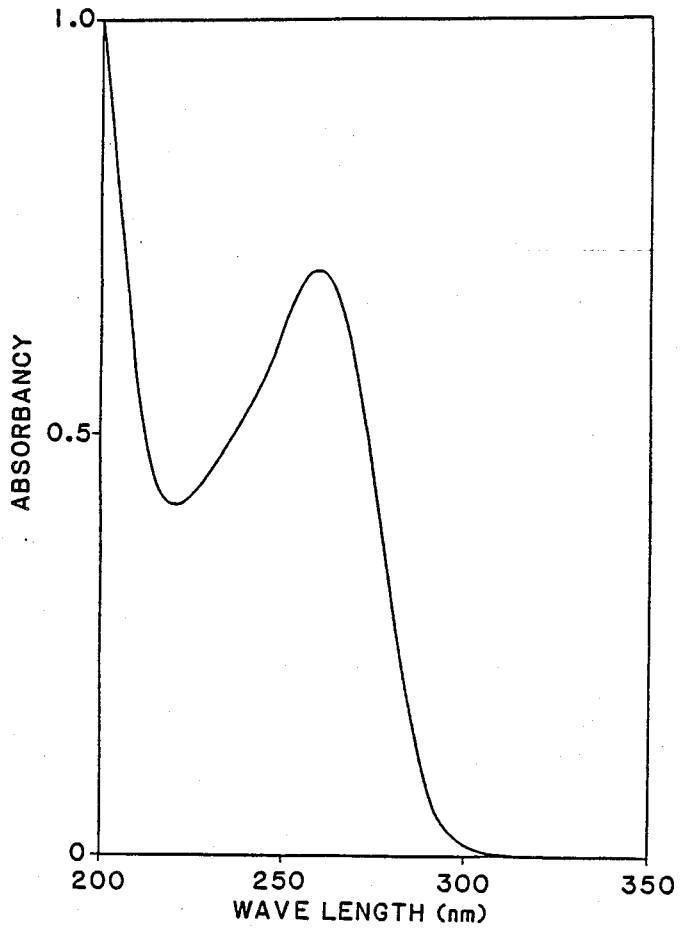
Figure 5:
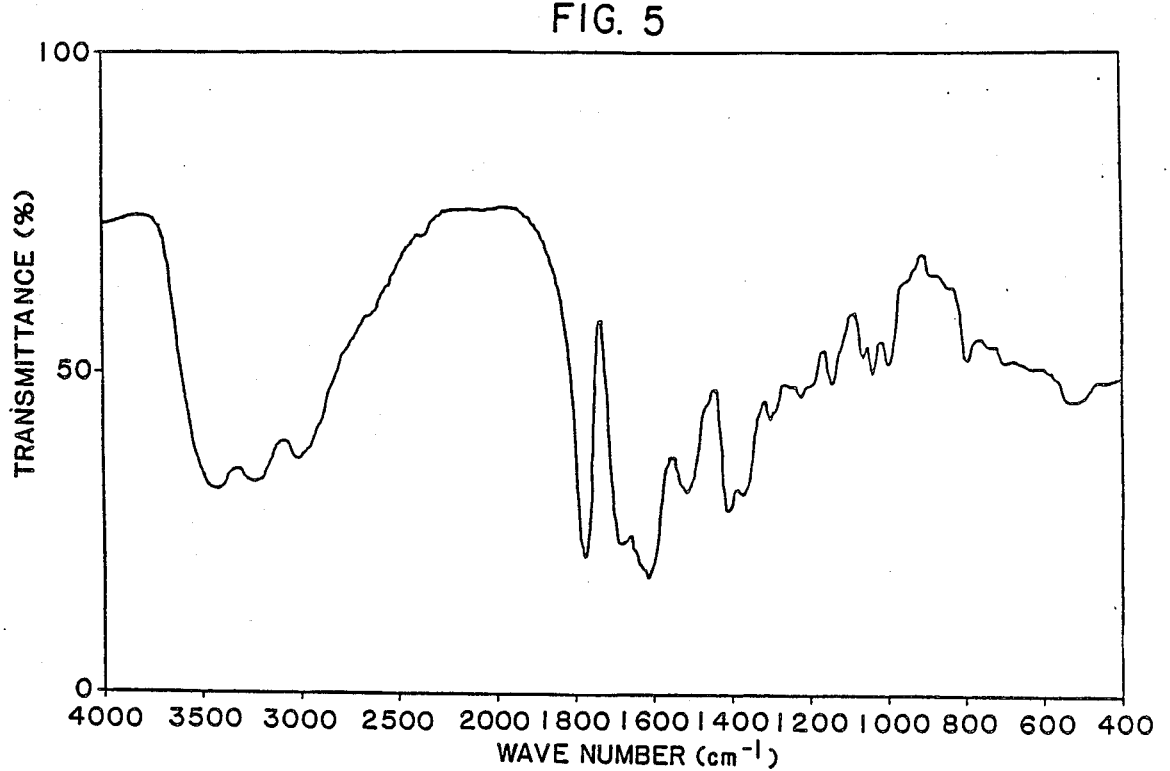
Figure 6:
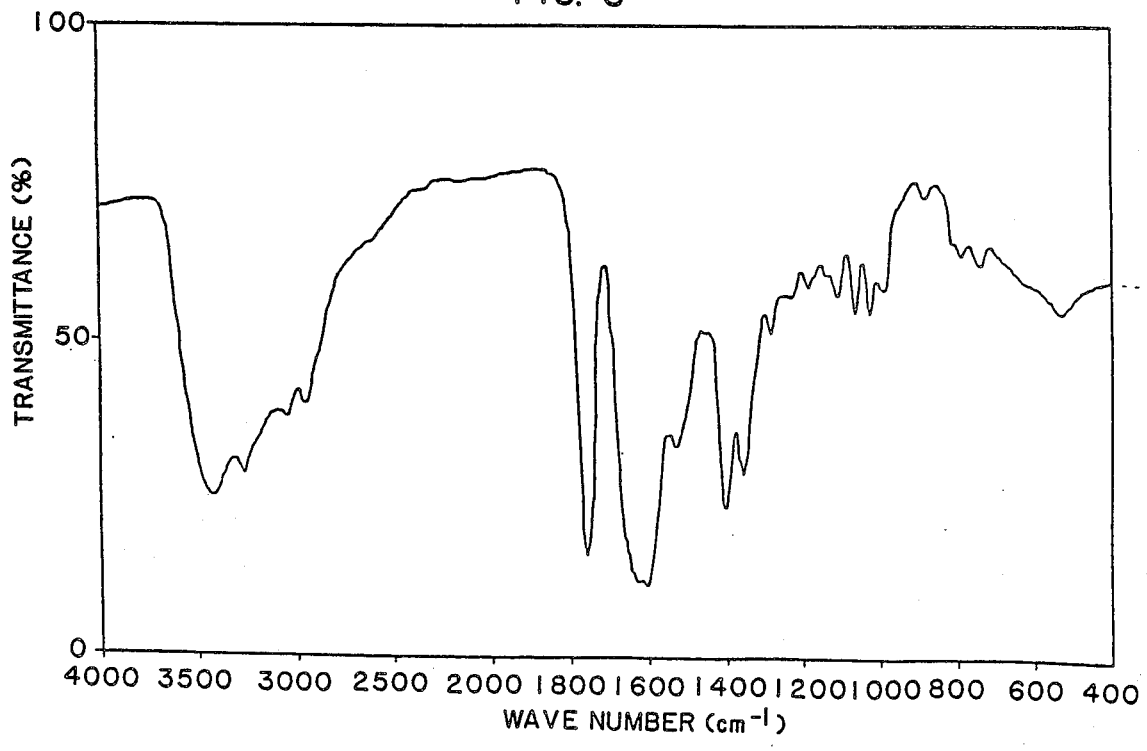
Figure 7:
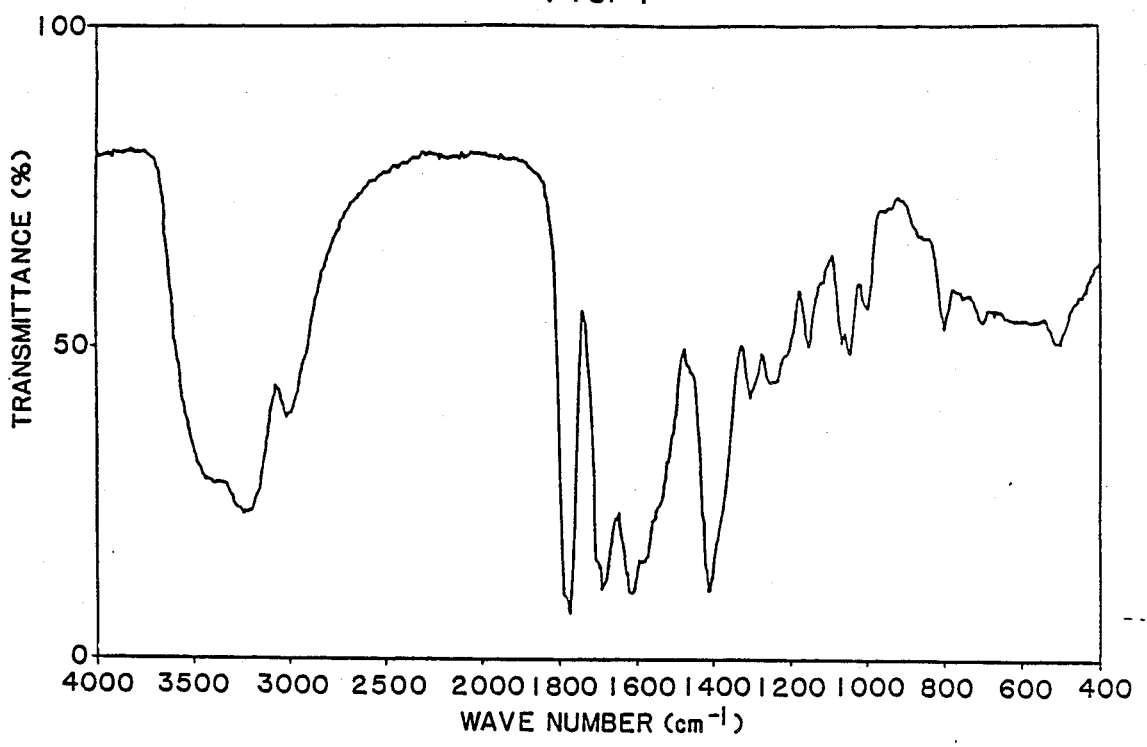
Figure 8:
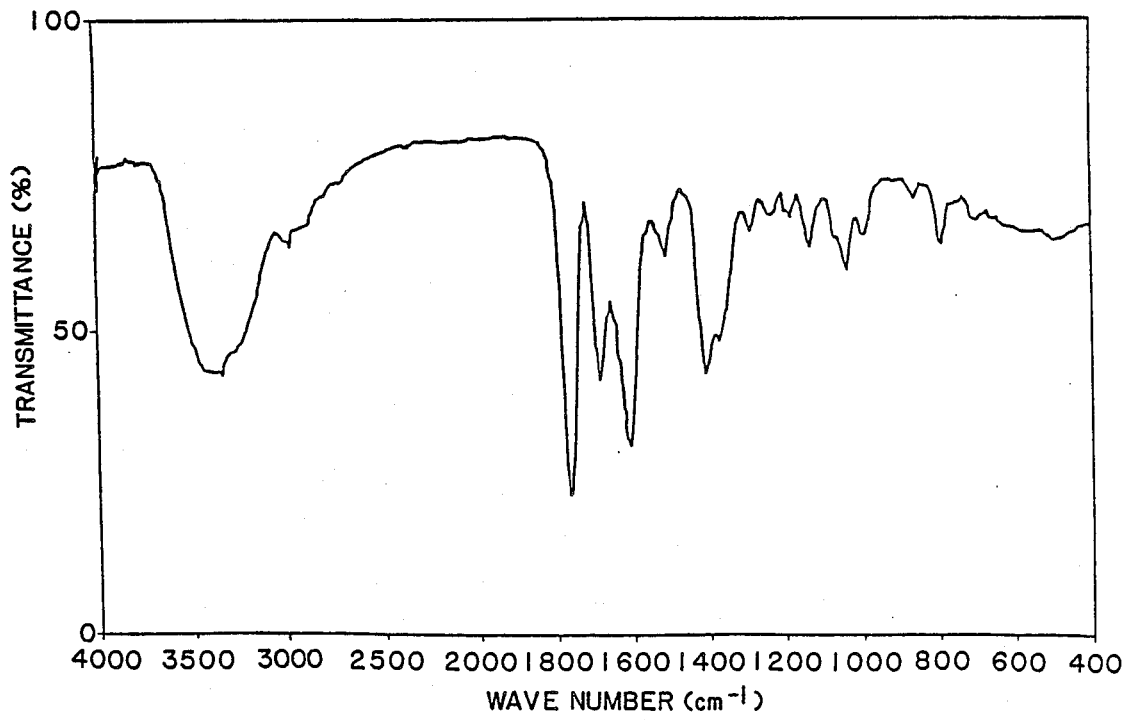

(6) UV spectrum: FIG. 3

$$\lambda_{max}^{H_2O} 260 \pm 2 \text{ nm } (E_{1\,cm}^{1\%} = 113 \pm 20)$$

(7) CD spectrum:

$$[\theta]_{228 \pm 2}^{H_2O} - 33600 \pm 5000$$

and $$[\theta]_{260 \pm 2}^{H_2O} + 30700 \pm 5000$$

(8) IR spectrum: Main wave numbers (cm$^{-1}$) are shown below:
3370, 3260, 3220, 3080, 3000, 1780, 1735, 1675, 1535, 1460, 1410, 1260, 1170, 1070, 880, 800, 530.

(9) $^{13}$C-NMR spectrum: in D$_2$O, Signals at 100 MHz are shown below (δ ppm).
179.78(s), 177.92(s), 176.88(s), 176.15(s), 173.49(s), 170.77(s), 166.41(d), 162.25(s), 159.59(s), 134.39(s), 118.69(s), 79.66(s), 72.91(d), 67.11(t), 66.04(d), 56.95(d), 56.03(d), 53.14(d), 51.72(d), 43.61(t), 41.52(t), 37.32(t), 32.62(t), 29.23(t), 28.66(t), 27.50(t), 23.47(t), 19.55(q), 19.51(q).

(10) Amino acid analysis: (the same conditions as that of A)
Alanine: 2.1 mole
α-aminoadipic acid: 1.1 mole

(11) TLC: (the same conditions as that of A) Rf=0.55

(12) HPLC: (the same conditions as that of A) Rt=6.8 (min)

(iii) TAN-547C.dihydrochloride
(1) Appearance: White powder
(2) Specific rotation:

$$[\alpha]_D^{25} + 25.1° \pm 15° \text{ (c=0.49 in water)}$$

(3) Molecular weight: SIMS method; (M+H)$^+$ 830
(4) Molecular formula: $C_{32}H_{51}N_{11}O_{13}S \cdot 2HCl \cdot (3H_2O)$
(5) Elemental analysis (%):

| Found*1 | Calcd.*2 |
|---|---|
| C, 39.61 ± 2.0 | C, 40.17 |
| H, 6.54 ± 1.0 | H, 6.22 |
| N, 15.92 ± 1.5 | N, 16.10 |
|  | O, 26.75 |
| S, 3.41 ± 1.0 | S, 3.35 |
| Cl, 6.41 ± 1.5 | Cl, 7.41 |

*1, *2 the same conditions as those of A.

(6) UV spectrum:

$$\lambda_{max}^{H_2O} 260 \pm 2 \text{ nm } (E_{1\,cm}^{1\%} = 106 \pm 20)$$

(7) CD spectrum:

$$[\theta]_{228 \pm 2}^{H_2O} - 34700 \pm 5000$$

and $$[\theta]_{260 \pm 2}^{H_2O} + 28400 \pm 5000$$

(8) IR spectrum: the main wave number (cm$^{-1}$) in KBr are as follows.
3350, 3250, 3070, 3000, 2950, 1780, 1735, 1665, 1530, 1450, 1400, 1300, 1250, 1160, 1060, 790, 520.

(9) $^{13}$C-NMR spectrum: in D$_2$O, Signals at 100 MHz are shown below (δ ppm).
179.79(s), 178.04(s), 177.47(s), 177.38(s), 176.12(s), 173.47(s), 171.08(s), 166.32(d), 162.07(s), 159.52(s), 135.00(s), 117.27(s), 79.57(s), 72.86(d), 67.10(t), 65.88(d), 57.28(d), 55.87(d), 53.07(d), 52.35(d), 51.62(d), 43.52(t), 41.52(t), 37.27(t), 32.73(t), 29.25(t), 28.48(t), 27.36(t), 23.41(t), 19.45(q), 19.42(q), 19.25(q).

(10) Amino acid analysis: (the same conditions as that of A)
Alanine: 3.1 mole
α-aminoadipic acid: 1.1 mole

(11) TLC: (the same conditions as that of A) Rf=0.60
(12) HPLC: (the same conditions as that of A) Rt=11.7 (min.)

(iv) TAN-547D.hydrochloride
(1) Appearance: White powder
(2) Specific rotation:

$$[\alpha]_D^{25} + 53.5° \pm 10° \text{ (c=0.51, in water)}$$

(3) Molecular weight: SIMS method, (M+H)$^+$ 645
(4) Molecular formula: $C_{25}H_{40}N_8O_{10}S \cdot HCl \cdot (3H_2O)$
(5) Elemental analysis (%):

| Found*1 | Calcd.*2 |
|---|---|
| C, 40.30 ± 2.0 | C, 40.84 |
| H, 6.44 ± 1.0 | H, 6.44 |
| N, 15.34 ± 1.5 | N, 15.24 |
|  | O, 28.29 |
| S, 4.39 ± 1.0 | S, 4.36 |
| Cl, 4.66 ± 1.5 | Cl, 4.82 |

*1 The sample was dried over diphosphorus pentoxide for 15 hours at room temperature under reduced pressure.
*2 The value is calculated as the sample contains 3 moles of water.

(6) Ultraviolet absorption (UV) spectrum:

$$\lambda_{max}^{H_2O} 260 \pm 2 \text{ nm } (E_{1\,cm}^{1\%} = 122 \pm 20)$$

(7) Circular dichromatic spectrum (CD) spectrum:

$$[\theta]_{226 \pm 2}^{H_2O} - 33000 \pm 5000$$

and $$[\theta]_{258 \pm 2}^{H_2O} + 21000 \pm 5000$$

(—: negative (—) Cotton effect; +: positive (+) Cotton effect)

(8) Infrared absorption spectrum: Main wave number (cm$^{-1}$) in KBr tablet.
3400, 3250, 3075, 2950, 1765, 1735, 1665, 1540, 1450, 1400, 1350, 1270, 1160, 1115, 1065, 1030, 980, 750, 540.

(9) Nuclear magnetic resonance ($^{13}$C-NMR) spectrum: in D$_2$O, signals at 100 MHz are shown below (δ ppm):
179.52(s), 177.43(s), 176.05(s), 173.72(s), 171.61(s), 167.89(s), 159.57(s), 134.40(s), 118.99(s), 72.64(d), 67.23(t), 61.99(d), 60.13(d), 57.32(d), 56.28(d), 51.97(d), 43.53(t), 41.18(t), 37.58(t), 32.75(t), 28.94(t), 28.43(t), 27.46(t), 23.85(t), 19.70(q).

(10) Amino acid analysis: in 5.5N-HCl, 110° C., the sample was hydrolized for 15 hours.
Alanine: about 1 mole
α-Aminoadipic acid: about 1 mole

(11) Thin layer chromatography (TLC): spot film, cellulose (Tokyo Chemical Industries, Ltd., Japan) Solvent system, acetonitrile: 3% ammonium sulfate (1:1), Rf=0.50

(12) High performance liquid chromatography (HPLC): column, YMC pack A312, mobil phase 5% methanol/0.01M phosphate buffer (pH 3.0), 2 ml/min. Rt=4.2 (min)

The following properties are in common among the components D, E and F (as hydrochloride(s)).

(13) Solubility:
Easily soluble: water, aqueous acetone, aqueous alcohol,
Sparingly soluble: dimethylsulfoxide, methanol, acetone, ethyl acetate

(14) Color reaction:
Positive: ninhydrine, Greig-Lieback, Sakaguchi reactions Negative: Ehrlich, Barton reactions, potassium permanganate

(15) Stability:
Slightly unstable in acidic or neutral aqueous solution. Unstable in basic aqueous solution.

(16) Properties of the substance:
Amphoteric substance (dihydrochloride is neutral).

(v) TAN-547E.dihydrochloride
(1) Appearance: White powder
(2) Specific rotation:

$[\alpha]_D^{25} + 31.1° \pm 10°$ (c=0.51 in water)

(3) Molecular weight: SIMS method, $(M+H)^+ 716$
(4) Molecular formula: $C_{28}H_{45}N_9O_{11}S \cdot 2HCl \cdot (3H_2O)$
(5) Elemental analysis (%):

| Found*1 | Calcd.*2 |
|---|---|
| C, 39.86 ± 2.0 | C, 39.90 |
| H, 6.28 ± 1.0 | H, 6.34 |
| N, 14.64 ± 1.5 | N, 14.96 |
|  | O, 26.58 |
| S, 3.79 ± 1.0 | S, 3.80 |
| Cl, 7.83 ± 1.5 | Cl, 8.41 |

*1, *2 The same conditions as those of D.

(6) UV spectrum:

$\lambda_{max}^{H_2O} 260 \pm 2$ nm ($E_1 {}_{cm}^{1\%} = 114 \pm 20$)

(7) CD spectrum:

$[\theta]_{226\pm2}^{H_2O} -31000 \pm 5000$ and $[\theta]_{256\pm2}^{H_2O} +21000 \pm 5000$ (8) IR spectrum: Main wave number (cm⁻¹) are shown below.
3375, 3260, 3220, 3075, 2950, 1770, 1735, 1660, 1540, 1455, 1400, 1345, 1250, 1160, 1115, 1065, 1035, 980, 880, 815, 540.

(9) ¹³C-NMR spectrum: in D₂O, the signals at 100 MHz are shown below (δ ppm)

179.48(s), 177.82(s), 177.36(s), 176.12(s), 173.46(s), 171.49(s), 167.83(s), 159.54(s), 134.37(s), 118.99(s), 72.84(d), 67.19(t), 61.95(d), 60.10(d), 57.31(d), 55.96(d), 53.04(d), 51.63(d), 43.53(t), 41.47(t), 37.53(t), 32.72(t), 29.14(t), 28.38(t), 27.43(t), 23.81(t), 19.44(q) (two occurrences).

(10) Amino acid analysis: (the same conditions as those of D)
Alanine: about 2 moles
α-aminoadipic acid: about 1 mole

(11) TLC: (the same conditions as those of D)
Rf=0.54

(12) HPLC: (the same conditions as those of D)
Rt=4.9 (min)

(vi) TAN-547F.dihydrochloride
(1) Appearance: White powder
(2) Specific rotation:

$[\alpha]_D^{25} + 5.8° \pm 3°$ (c=0.49, in water)

(3) Molecular weight: SIMS method, $(M+H)^+ 787$
(4) Assumed molecular formula: $C_{31}H_{50}N_{10}O_{12}S \cdot 2HCl \cdot (3H_2O)$
(5) Elemental analysis:

| (%) | |
|---|---|
| Found*1 | Calcd.*2 |
| C, 40.27 ± 2.0 | C, 40.74 |
| N, 14.52 ± 1.5 | N, 15.33 |
|  | O, 26.26 |
| S, 2.92 ± 1.0 | S, 3.51 |
| Cl, 7.12 ± 1.5 | Cl, 7.76 |

*1, *2 the same conditions as those of D.

(6) UV spectrum:

$\lambda_{max}^{H_2O} 260 \pm 2$ nm ($E_1 {}_{cm}^{1\%} = 94 \pm 20$)

(7) CD spectrum:

$[\theta]_{226\pm2}^{H_2O} -30000 \pm 5000$ and $[\theta]_{258\pm2}^{H_2O} +17000 \pm 5000$ (8) IR spectrum: the main wave number (cm⁻¹) in KBr are as follows:
3360, 3250, 3070, 3000, 2950, 1770, 1735, 1660, 1535, 1455, 1395, 1345, 1240, 1160, 1115, 1065, 1030, 980, 960, 870, 510.

(9) ¹³C-NMR spectrum: in D₂O, Signals at 100 MHz are shown below (δ ppm)
179.39(s), 177.87(s), 177.26(s), 176.47(s), 176.15(s), 173.45(s), 170.68(s), 168.00(s), 159.65(s), 133.51(s), 121.03(s), 72.90(d), 67.15(t), 62.04(d), 60.21(d), 56.84(d), 55.91(d), 53.02(d), 52.44(d), 51.77(d), 43.64(t), 41.54(t), 37.47(t), 32.54(t), 29.30(t), 28.56(t), 27.41(t), 23.77(t), 19.55(q), 19.44(q), 19.37(q).

(10) Amino acid analysis: (the same conditions as those of D)
Alanine: about 3 moles
α-aminoadipic acid: about 1 mole

(11) TLC: (the same conditions as those of D)
Rf=0.58

(12) HPLC: (the same conditions as those of D)
Rt=6.5 (min)

In said properties, the absolute configurations of alanine and α-aminoadipic acid were determined by HPLC method as the L-form and D-form, respectively.

REFERENCE EXAMPLE 2

(1) *Xanthomonas lactamgena* YK-280 (IFO 14330, FERM BP-635) isolated from a plant sample collected at Tsuge, Ayama District, Mie Prefecture, Japan, which was grown on a nutrient agar slant, was used to inoculate a 2-l Sakaguchi flask containing 500 ml of a culture medium comprising an aqueous solution (pH 7.0) having the composition of 2% of glucose, 3% of soluble starch, 1% of raw soybean flour, 0.3% of corn steep liquor, 0.5% of Polypepton and 0.3% of sodium chloride and 0.5% of precipitating calcium carbonate admixed, and incubated on a reciprocating shaker at 24° C. for 48 hours. The total volume of the culture broth thus obtained was transferred to a tank with a 200 l capacity containing 120 l of the above-described culture medium admixed with 0.05% of an antifoam, Actcol, and incubated at 24° C. for 48 hours, with aeration at the rate of 120 l/min and agitation at 120 r.p.m. The total volume of the culture broth was transferred to a tank with a 2000 l capacity containing 1200 l of culture medium comprising an aqueous solution (whose pH was not adjusted) having the composition of 3% of dextrin, 3% of raw soybean flour and 0.2% of Polypepton admixed with 0.5% of precipitating calcium carbonate and 0.05% of Actcol, and incubated at 24° C. for 66 hours, with aeration at the rate of 1200 l/min. and agitation at 100 r.p.m.

The culture (1140 l) obtained by the above procedure was adjusted at pH 6.0 with 2N hydrochloric acid, admixed with Hyflo-Super Cel, filtered and washed with water to yield a filtrate (1370 l). The filtrate was adjusted to pH 6.3, and passed through a column packed with Dowex-50W (Na+ type 50 to 100 mesh, 25 l). After the column was washed with water ((75 l), elution was conducted with 2M aqueous sodium chloride solution. The eluate was passed through a column packed with activated carbon (15 l), and after the column was washed with water (45 l), elution was carried out with 8% isobutanol-N/100 hydrochloric acid (105 l). The eluate was adjusted to pH 6.2 and concentrated to 12 l, and the concentrate was adjusted to pH 7.3 and passed through a column packed with Diaion HP-20 (10 l). The column was washed with 0.01M phosphate buffer (pH 7.3, 20 l), and elution was conducted with 0.01M phosphate buffer (pH 2.5, 100 l).

The eluate was passed through a column of activated carbon (2.5 l) and washed with water (6 l), and elution was carried out with 8% isobutanol-N/200 hydrochloric acid (18 l). The eluate was concentrated to 1.6 l, and the concentrate was adjusted to pH 7.3 and passed through a column packed with Diaion HP-20 (50 to 100 mesh, 2 l). The column was washed with 0.01M pohsphate buffer (pH 7.3, 4 l), and elution fractionation was conducted with 0.01M phosphate buffer (pH 3.0, 20 l). Individual fractions were subjected to analysis by liquid chromatography, and separated into two groups of fractions containing TAN-592A, B and C as a principal component and fractions containing TAN-592D, E and F as a principal component.

The fractions containing TAN-592A, B and C as a principal component as obtained in the above were collected and passed through a column of activated carbon (500 ml), and after the column was washed with water (1.5 l), elution was conducted with 8% isobutanol-N/200 hydrochloric acid (3 l). After the eluate was concentrated, the concentrate was passed through a column packed with CM-Sephadex C-25 (Na+ type, 0.8 l), and elution fractionation was carried out with 0.02M aqueous sodium chloride solution (40 l). Individual fractions were subjected to analysis by liquid chromatography, and the fractions showing a single peak of TAN-592A and B, respectively, and the fractions containing TAN-512C as a principal component were collected.

The fractions containing TAN-592A solely were collected and passed through a column of activated carbon (0.3 l), and after the column was washed with water (0.9 l), elution was carried out with 8% isobutanol-N/200 hydrochloric acid (2.1 l). The eluate was concentrated, and the concentrate was lyophilized to give a white powder (1.5 g) of TAN-592 dihydrochloride. In the same manner as described above, there were obtained a white powder (2.0 g) of TAN-592B monohydrochloride from the fractions containing TAN-592B solely and a crude powder (1.9 g) of TAN-592C from the fractions containing TAN-592C as a principal component.

The crude powder (0.7 g) of TAN-592C was passed through a column packed with CM-Sephadex C-25 (Na+ type, 100 ml), and elution fractionation was carried out with 0.02M aqueous sodium chloride solution (3 l). Individual fractions were subjected to analysis by liquid chromatography, and the fractions containing TAN-592 as a principal component were collected and passed through a column of activated carbon (30 ml). After the column was washed with water (100 ml), elution was conducted with 8% isobutanol-N/200 hydrochloric acid (210 ml), and the eluate was concentrated.

The concentrate was subjected to HPLC for separation with use of YMC-Pack SH-343 (20 mm $\phi \times 250$ mm, produced by Yamamura Chemical Laboratories), and elution was carried out with 0.01M phosphate buffer (pH 3.0). Individual fractions were subjected to analysis by liquid chromatography, and the fractions showing a single peak were collected. The effective fractions were adjusted to pH 7.3 with 1N NaOH, readjusted to pH 3.0 with 1N HCl and passed through a column packed with activated carbon (20 ml). After the column was washed with water (80 ml), elution was carried out with 8% isobutanol-water (200 ml), and the eluate was concentrated and lyophilized to give a white powder (110 mg) of TAN-592C dihydrochloride.

The fractions containing TAN-592D, E and F as a principal component as obtained in the above were collected and passed through a column of activated carbon (200 ml), and after the column was washed with water(600 ml), elution was carried out with 8% isobutanol-N/200 hydrochloric acid (1.4 l). After the eluate was concentrated, the concentrate was passed through a column packed with CM-Sephadex C-25 (Na+ type, 300 ml), and elution fractionation was conducted with 0.02M aqueous sodium chloride solution (15 l). Individual fractions were subjected to analysis by liquid chromatography, and the fractions containing TAN-592D, E and F as a principal component, respectively, were collected.

The fractions containing TAN-592D as a principal component were collected, and passed through a column of activated carbon (80 ml), and after the column was washed with water (250 ml), elution was carried out with 8% isobutanol-N/200 hydrochloric acid (560 ml). The eluate was concentrated and the concentrate was lyophilized to give a crude powder (1236 mg) of TAN-592D. By conducting the same procedure with the fractions containing TAN-592E and F as a principal component, respectively, there were obtained a crude powder (1560 mg) of TAN-592E and a crude powder (656 mg) of TAN-592F.

The crude powder (1236 mg) of TAN-592D was subjected to high performance liquid chromatography for separation with use of YMC-Pack SH-343, and elution fractionation was carried out with 1% methanol-0.01M phosphate buffer (pH 3.0). Individual fractions were subjected to analysis by liquid chromatography, and the fractions showing a single peak were collected. The effective fractions were adjusted to pH 7.3 with 1N NaOH, readjusted to pH 3.0 with 1N HCl and passed through a column packed with activated carbon (50 ml), and after the column was washed with water (200 ml), elution was conducted with 8% aqueous isobutanol (400 ml). The eluate was concentrated, and the concentrate was lyophilized to yield a white powder (332 mg) of TAN-592D dihydrochloride.

In the same manner as described above, the crude powders of TAN-592E and F were subjected to high performance liquid chromatography for separation to give a white powder (501 mg) of TAN-592E dihydrochloride and a white powder (46 mg) of TAN-592F dihydrochloride, respectively.

The physico-chemical properties of Antibiotic TAN-592.hydrochloride obtained in the above are shown below.

(i) TAN-592A.dihydrochloride:
(1) Appearance: white powder
(2) Molecular weight: SIMS method, $(M+H)^+$ 704
(3) Molecular formula: $C_{26}H_{41}N_9O_{12}S \cdot 2HCl \cdot (2H_2O)$
(4) Elemental analysis (%):

| Found*[1] | Calcd.*[2] |
|---|---|
| C, 38.49 ± 2.0 | C, 38.43 |
| H, 6.03 ± 1.0 | H, 5.83 |
| N, 15.63 ± 1.5 | N, 15.51 |
|  | O, 27.56 |
| S, 4.22 ± 1.0 | S, 3.95 |
| Cl, 7.95 ± 1.5 | Cl, 8.73 |

*[1] The sample was dried over diphosphorus pentoxide for 8 hours at 60° C. under reduced pressure.
*[2] The value is calculated as the sample contains 2 moles of water.

(5) Ultraviolet absorption (UV) spectrum:

$\lambda_{max}^{H2O}$ 260±2 nm ($E_1 \text{ cm}^{1\%} = 124 \pm 20$)

(6) Circular dichroism (CD) spectrum:

$[\theta]_{226\pm2}^{H2O} - 32000 \pm 5000$ and $[\theta]_{258\pm2}^{H2O} + 28000 \pm 5000$ (7) Infrared absorption (IR) spectrum: Main wave number ($cm^{-1}$) in KBr tablet:
3420, 3080, 2960, 1780, 1730, 1670, 1510, 1400, 1260, 1170, 1060, 980, 860, 510.

(8) Nuclear magnetic resonance ($^{13}$C-NMR) spectrum: in $D_2O$, signals at 100 MHz are shown below (δppm).
179.79(s), 177.00(s), 176.11(s), 170.93(s), 170.77(s), 166.42(d), 162.24(s), 159.63(s), 134.46(s), 118.40(s), 79.67(s), 72.70(d), 67.07(t), 66.01(d), 63.26(t), 57.58(d), 57.03(d), 56.52(d), 43.61(t), 41.18(t), 37.35(t), 32.68(t), 28.98(t), 28.65(t), 27.52(t), 23.50(t).

(s: singlet, d: doublet, t: triplet, q: quartet)

(9) Amino acid analysis: in 5.5N-HCl, 110° C., the sample was hydrolized for 15 hours. Serine and α-aminoadipic acid were detected.

(10) Thin layer chromatography (TLC): Spot film cellulose (Tokyo Chemical Industries, Ltd., Japan)
Solvent system, acetonitrile: 3% ammonium sulfate (1:1), Rf=0.58

(11) High performance liquid chromatography (HPLC): column, YMC pack A312,
mobil phase, 2% methanol/0.01
M phosphate buffer (pH 3.0), 2 ml/min. Rt=3.7 (min)

The following properties are in common among the components A, B, C, D, E and F.

(12) Solubility:
Easily soluble: water, aqueous acetone, aqueous alcohol Sparingly soluble: dimethylsulfoxide, methanol, acetone, ethyl acetate

(13) Color reaction:
Positive: ninhydrin, Greig-Leaback, Sakaguchi reactions
Negative: Barton reaction, potassium permanganate (ii) TAN-592B.monohydrochloride
(1) Appearance: white powder
(2) Molecular weight: SIMS method, $(M+H)^+$ 791
(3) Molecular formula: $C_{29}H_{46}N_{10}O_{14}S \cdot HCl \cdot (2H_2O)$
(4) Elemental analysis (%):

| Found*[1] | Calcd.*[2] |
|---|---|
| C, 40.00 ± 2.0 | C, 40.35 |
| H, 5.83 ± 1.0 | H, 5.95 |
| N, 15.64 ± 1.5 | N, 16.23 |
|  | O, 29.65 |
| S, 4.30 ± 1.0 | S, 3.71 |
| Cl, 4.53 ± 1.5 | Cl, 4.11 |

*[1], *[2] The same conditions as those of A.

(5) UV spectrum:

$\lambda_{max}^{H2O}$ 260±2 nm ($E_1 \text{ cm}^{1\%} = 108 \pm 20$)

(6) CD spectrum:

$[\theta]_{226\pm2}^{H2O} - 31000 \pm 5000$ and $[\theta]_{258\pm2}^{H2O} + 29000 \pm 5000$ (7) IR spectrum:
3400, 3080, 2950, 1780, 1730, 1660, 1520, 1390, 1250, 1170, 1060, 980, 860, 520.

(8) $^{13}$C-NMR spectrum:
179.85(s), 177.20(s), 176.24(s), 174.41(s), 171.13(s), 166.42(d), 162.23(s), 159.61(s), 134.55(s), 117.97(s), 79.67(s), 72.86(d), 67.10(t), 66.00(d), 63.89(t), 63.19(t), 59.10(d), 57.40(d), 57.18(d), 56.30(d), 43.58(t), 41.46(t), 37.36(t), 32.74(t), 29.33(t), 28.66(t), 27.41(t), 23.52(t).

(9) Amino acid analysis: (the same conditions as that of A)
Serine (about 2 moles) and α-aminoadipic acid were detected.

(10) TLC: (the same conditions as that of A) Rf=0.61
(11) HPLC: (the same conditions a that of A) Rt=4.2 (min.)

(iii) TAN-592C.dihydrochloride
(1) Appearance: white powder
(2) Molecular weight: SIMS method, $(M+H)^+$ 862
(3) Molecular formula: $C_{32}H_{51}N_{11}O_{15}S \cdot 2HCl \cdot (4H_2O)$
(4) Elemental analysis (%):

| Found*1 | Calcd.*2 |
|---|---|
| C, 38.04 ± 2.0 | C, 38.17 |
| H, 6.30 ± 1.0 | H, 6.11 |
| N, 14.30 ± 1.5 | N, 15.30 |
|  | O, 30.19 |
| S, 3.18 ± 1.0 | S, 3.18 |
| Cl, 7.76 ± 1.5 | Cl, 7.04 |

*1 The same conditions as those of A.
*2 The sample contains 4 moles of water.

(5) UV spectrum:

$\lambda_{max}^{H2O}\ 260 \pm 2$ nm ($E_{1\ cm}^{1\%} = 97 \pm 20$)

(6) CD spectrum:

$[\theta]_{226 \pm 2}^{H2O} - 28000 \pm 5000$ and $[\theta]_{258 \pm 2}^{H2O} + 26000 \pm 5000$ (7) IR spectrum:
3420, 3070, 3000, 2950, 1780, 1735, 1660, 1520, 1450, 1390, 1250, 1165, 1060, 860, 520.

(8) $^{13}$C-NMR spectrum:
179.52(s), 178.64(s), 176.16(s), 175.71(s), 174.49(s), 173.94(s), 169.48(s), 166.45(d), 162.54(s), 159.67(s), 132.57(s), 123.59(s), 79.79(s), 72.33(d), 66.82(t), 66.47(d), 64.06(t), 63.87(t), 58.97(d), 58.28(d), 56.26(d), 56.21(d), 51.93(d), 43.62(t), 41.46(t), 37.25(t), 32.33(t), 29.33(t), 28.91(t), 27.35(t), 23.41(t), 19.47(q).

(9) Amino acid analysis: (the same conditions as that of A)

Serine (about 2 moles), alanine and α-aminoadipic acid were detected.

(10) TLC: (the same conditions as that of A)
Rt=0.68

(11) HPLC: (the same conditions as that of A)
Rt=4.6 (min.)

(iv) TAN-592D.dihydrochloride
(1) Appearance: white powder
(2) Molecular weight: SIMS method, (M+H)+ 661
(3) Molecular formula: $C_{25}H_{40}N_8O_{11}S \cdot 2HCl \cdot (3H_2O)$
(4) Elemental analysis:

| Found*1 | Calcd.*1 |
|---|---|
| C, 37.51 ± 2.0 | C, 38.12 |
| H, 6.28 ± 1.0 | H, 6.14 |
| N, 14.10 ± 1.5 | N, 14.23 |
|  | O, 28.44 |
| S, 4.00 ± 1.0 | S, 4.07 |
| Cl, 9.94 ± 1.5 | Cl, 9.00 |

*1 The same conditions as those of A.
*2 The sample contains 3 moles of water.

(5) UV spectrum:

$\lambda_{max}^{H2O}\ 260 \pm 2$ nm ($E_{1\ cm}^{1\%} = 110 \pm 20$)

(6) CD spectrum:

$[\theta]_{226 \pm 2}^{H2O} - 25000 \pm 5000$ and $[\theta]_{256 \pm 2}^{H2O} + 22000 \pm 5000$ (7) IR spectrum:
3420, 3075, 2950, 1770, 1735, 1670, 1550, 1460, 1400, 1260, 1170, 1110, 1065, 870, 540.

(8) $^{13}$C-NMR spectrum:
179.36(s), 176.10(s), 175.86(s), 170.69(s), 170.18(s), 168.18(s), 159.69(s), 132.59(s), 122.91(s), 72.69(d), 67.04(t), 63.21(t), 62.08(d), 60.24(d), 57.58(d), 56.57(d), 56.39(d), 43.64(t), 41.19(t), 37.41(t), 32.36(t) 28.97(t), 28.71(t), 27.51(t), 23.71(t).

(9) Amino acid analysis: (the same conditions as those of A)

Serine and α-aminoadipic acid were detected.

(10) TLC: (the same conditions as those of A)
Rf=0.62

(11) HPLC: (the same conditions as those of A)
Rt=7.9 (min.)

(v) TAN-592E.dihydrochloride
(1) Appearance: white powder
(2) Molecular weight: SIMS method, (M+H)+ 748
(3) Molecular formula: $C_{28}H_{45}N_9O_{13}S \cdot 2HCl \cdot (H_2O)$
(4) Elemental analysis:

| Found*1 | Calcd.*2 |
|---|---|
| C, 39.71 ± 2.0 | C, 40.10 |
| H, 5.87 ± 1.0 | H, 5.89 |
| N, 14.85 ± 1.5 | N, 15.03 |
|  | O, 26.71 |
| S, 3.90 ± 1.0 | S, 3.82 |
| Cl, 7.46 ± 1.5 | Cl, 8.45 |

*1 The same conditions as those of A.
*2 The sample contain 1 mole of water.

(5) UV spectrum:
$\lambda_{max}^{H2O}\ 260 \pm 2$ nm ($E_{1\ cm}^{1\%} = 91 \pm 20$)

(6) CD spectrum $[\theta]_{226 \pm 2}^{H2O} - 24000 \pm 5000$ and $[\theta]_{256 \pm 2}^{H2O} + 17000 \pm 5000$ (7) IR spectrum:
3400, 3060, 2950, 1765, 1730, 1660, 1540, 1460, 1390, 1240, 1170, 1110, 1060, 1020, 870, 810, 500.

(8) $^{13}$C-NMR spectrum
179.41(s), 176.44(s), 176.20(s), 174.23(s), 171.02(s), 168.01(s), 159.66(s), 133,50(s), 121.05(s), 72.83(d), 67.11(t), 63.92(t), 63.12(t), 62.06(d), 60.21(d), 58.99(d), 57.38(d), 56.82(d), 56.27(d), 43.62(t), 41.40(t), 37.49(t), 32.54(t), 29.23(t), 28.59(t), 27.40(t), 23.78(t).

(9) Amino acid analysis: (the same conditions as those of A)

Serine (about 2 moles) and α-aminoadipic acid were detected.

(10) TLC: (the same conditions as those of A)
Rf=0.64

HPLC: (the same conditions as those of A)
Rt=9.6 (min.)

(vi) TAN-592F.dihydrochloride
(1) Appearance: white powder
(2) Molecular weight: SIMS method, (M+H)+ 819
(3) Molecular formula: $C_{31}H_{50}N_{10}O_{14}S \cdot 2HCl \cdot (4H_2O)$
(4) Elemental analysis (%):

| Found*1 | Calcd.*2 |
|---|---|
| C, 38.00 ± 2.0 | C, 38.63 |
| H, 6.87 ± 1.0 | H, 6.27 |
| N, 14.35 ± 1.5 | N, 14.53 |
|  | O, 29.88 |
| S, 3.10 ± 1.0 | S, 3.33 |

-continued

| Found[*1] | Calcd.[*2] |
|---|---|
| Cl, 7.78 ± 1.5 | Cl, 7.36 |

[*1] The same conditions as those of A.
[*2] The sample contains 4 moles of water.

(5) UV spectrum:

$\lambda_{max}^{H2O}$ 260±2 nm ($E_{1\ cm}^{1\%}$=90±20)

(6) CD spectrum:

$[\theta]_{226\pm 2}^{H2O}$ −32000±5000 and $[\theta]_{256\pm 2}^{H2O}$ +20000±5000

(7) IR spectrum:
3420, 3070, 2950, 1770, 1735, 1660, 1540, 1460, 1395, 1340, 1250, 1160, 1110, 1065, 530.
(8) Amino acid analysis: (the same conditions as those of A)
Serine (about 2 moles), alanine and α-aminoadipic acid were detected.
(9) TLC: (the same conditions as those of A)
Rf=0.67
(10) HPLC: (the same conditions as those of A)
Rt=10.1 (min.)

In said properties, the absolute configurations of serine, alanine and α-aminoadipic acid were determined by HPLC as the L-form, L-form and D-form, respectively.

(2) A culture of *Xanthomonas lactamgena* YK-278 (IFO 14351, FERM BP-636) grown on a nutrient agar slant was used to inoculate 15 Erlenmeyer flasks of a 200-ml capacity each containing 40 ml of a culture medium comprising of an aqueous solution (pH 7.0) having the composition of 2% of glucose, 3% of soluble starch, 1% of raw soybean flour, 0.3% of corn steep liquor, 0.5% of Polypepton and 0.3% of sodium chloride admixed with 0.5% of precipitating calcium carbonate, and incubated on a rotary shaker at 24° C. for 24 hours to make the resulting culture broth a seed culture.

16 l of a culture medium containing 3.0% of dextrin, 1.5% of corn gluten meal, 0.2% of Polypepton, 0.1% of sodium thiosulfate and 0.5% of precipitating calcium carbonate (pH 7.0) was distributed in 40 ml portions into Erlenmeyer flasks of a 200-ml capacity and sterilized at 120° C. for 20 minutes. 1 ml of the seed culture was used to inoculate the individual Erlenmeyer flasks each containing the sterilized culture medium, and incubated on a rotary shaker at 17° C. for 90 hours with the agitation at a rate of 230 r.p.m.

The culture broth (16 l) as obtained in the above manner was adjusted to pH 6.5 with 2N hydrochloric acid, admixed with water (16 l) and centrifuged to give a filtrate (32 l).

The filtrate was passed through a column packed with Dowex-50 W (Na+ type, 50 to 100 mesh, 0.5 l), and after the column was washed with water (1.5 l), elution was carried out with 2M aqueous sodium chloride solution (10 l). The eluate was passed through a column of activated carbon (0.3 l), and after the column was washed with water (1 l), elution was carried out 8% isobutanol-N/200 hydrochloric acid (2.2 l). The eluate was adjusted to pH 6.2 and concentrated to 0.5 l, and the concentrate was adjusted to pH 7.3 and passed through a column packed with Diaion HP-20 (0.6 l). The column was washed with 0.01M phosphate buffer (pH 7.3, 1.6 l), and elution was carried out with 0.01M phosphate buffer (pH 3.0, 6 l).

The three portions of eluates were respectively passed through a column of activated carbon (80 ml), and after the column was washed with water (300 ml), elution was carried out with 8% isobutanol-N/200 hydrochloric acid (600 ml). The eluate was lyophilized to give crude substances I (402 mg), II (760 mg) and III (448 mg).

It was confirmed by HPLC that in the crude substance II, there was included TAN-592A, B and C, in the crude substance III, there was included TAN-592D, E and F.

The crude substances were purified by the manner of the above (1) to give 18 mg of TAN-592 (hydrochloride), 39 mg of B, 35 mg of C, 12 mg of D, 15 mg of E and 24 mg of F.

The crude substance I (400 mg) was dissolved in water (100 ml), and the solution was passed through a column packed with CM-Sephadex C-25 (Na+ type, 50 ml), followed by elution fractionation with 0.02M aqueous sodium chloride solution (1.5 l). Individual fractions were subjected to analysis by liquid chromatography, and fractions containing TAN-591A, B and C as a principal component, respectively, were collected.

The fractions containing TAN-591A, B and C as a principal component, respectively, were passed through columns of activated carbon (10 ml for each column), and after the columns were washed with water (30 ml for each column), elution was effected with 8% aqueous isobutanol solutions (70 ml for each elution). The eluates were concentrated, and each concentrate was subjected to high performance liquid chromatography for separation using YMC-Pack SH-343 (20 mm φ×250 mm), followed by elution fractionation with 0.01M phosphate buffer (pH 4.5). Individual fractions were subjected to analysis by liquid chromatography, and fractions showing a single peak were collected. The effective fractions were adjusted to pH 7.3 with 1N NaOH, readjusted to pH 3.0 with 1N HCl and passed through a column packed with activated carbon (5 ml). After the column was washed with water (20 ml), elution was carried out with 8% aqueous isobutanol solution (50 ml), and the eluate was concentrated and lyophilized to give white powders of TAN-591A (3 mg), B (18 mg) and C (22 mg) hydrochlorides.

The physico-chemical properties of Antibiotic TAN-591.hydrochloride obtained in the above are shown bellow.

(i) TAN-591A.dihydrochloride
(1) Appearance: white powder
(2) Molecular weight: SIMS method, (M+H)+ 676
(3) Molecular formula: $C_{26}H_{41}N_7O_{12}S \cdot 2HCl \cdot (2H_2O)$
(4) Elemental analysis:

| Found[*1] | Calcd[*2] |
|---|---|
| C, 40.38 ± 2.0 | C, 39.79 |
| H, 6.53 ± 1.0 | H, 6.04 |
| N, 12.81 ± 1.5 | N, 12.50 |
|  | O, 28.54 |
| S, 4.07 ± 1.0 | S, 4.09 |
| Cl, 8.40 ± 1.5 | Cl, 9.04 |

[*1] The sample was dried over diphosphorus pentoxide for 8 hours at 60° C under reduced pressure.
[*2] C. The value is calculated as the sample contains 2 moles of water.

(5) Ultraviolet absorption (UV) spectrum:

$\lambda_{max}^{H2O}$ 260±2 nm ($E_{1\ cm}^{1\%}$=118±20)

(6) Circular dichloism (CD) spectrum:

$[\theta]_{226\pm2}^{H2O}$ −34000±5000 and $[\theta]_{258\pm2}^{H2O}$ +27000±5000

(7) Infrared (IR) spectrum: Main wave number (cm$^{-1}$) in KBr tablet,
3420, 3250, 3080, 2950, 1780, 1735, 1675, 1515, 1410, 1360, 1280, 1160, 1060, 980, 860, 520.

(8) Nuclear magnetic resonance ($^{13}$C-NMR) spectrum: in D$_2$O, signals at 100 MHz are shown below (δ ppm)
179.74(s), 177.19(s), 176.16(s), 170.90(s), 170.66(s), 166.42(d), 162.12(s), 134.89(s), 117.77(s), 79.70(s), 72.71(d), 67.12(t), 66.02(d), 63.22(t), 57.58(d), 57.35(d), 56.67(d), 42.22(t), 41.21(t), 37.36(t), 32.77(t), 31.28(t), 29.30(t), 28.62(t), 25.08(t), 23.50(t).

(s: singlet, d: doublet, t: triplet, q: quartet)

(9) Amino acid analysis: in 5.5 N-HCl, 110° C., the sample was hydrolized for 15 hours.
Serine and α-aminoadipic acid were detected.

(10) Thin layer chromatography (TLC): spot film, cellulose (Tokyo Chemical Industries, Ltd., Japan) Solvent system, acetonitrile: 3% ammonium sulfate (1:1), Rf=0.45

(11) High performance liquid chromatography (HPLC): column, YMC pack A312, mobile phase, 5% methanol/0.01M phosphate buffer (pH 3.0), 2 ml/min. Rt=2.4 (min.)

The following properties are in common among components A, B and C.

(12) Solubility:
Easily soluble: water, aqueous acetone, aqueous alcohol. Sparingly soluble: dimethylsulfoxide, methanol, acetone, ethyl acetate

(13) Color reaction:
Positive: Ninhydrine, Greig-Leaback reactions Negative: Barton reaction, potassium permanganate, Sakaguchi reaction (ii) TAN-591B. dihydrochloride
(1) Appearance: white powder
(2) Molecular weight: SIMS method, (M+H)$^+$763
(3) Molecular formula: $C_{29}H_{46}N_8O_{14}S.2HCl.(2H_2O)$
(4) Elemental analysis (%):

| Found*$^1$ | Calcd *$^2$ |
|---|---|
| C, 39.34 ± 2.0 | C, 39.95 |
| H, 6.02 ± 1.0 | H, 6.01 |
| N, 12.52 ± 1.5 | N, 12.85 |
|  | O, 29.38 |
| S, 4.40 ± 1.0 | S, 3.68 |
| Cl, 7.57 ± 1.5 | Cl, 8.13 |

*$^1$, *$^2$ The same conditions as those of A.

(5) UV spectrum $\lambda_{max}^{H2O}$ 260±2 nm ($E_{1cm}^{1\%}$=124±20)

(6) CD spectrum:

$[\theta]_{226\pm2}^{H2O}$ −39000±5000 and $[\theta]_{258\pm2}^{H2O}$ +29000±5000

(7) IR spectrum:
3400, 3270, 3080, 2970, 1780, 1735, 1670, 1530, 1410, 1260, 1160, 1060, 980, 875, 520.

(8) $^{13}$C-NMR spectrum:
179.69(s), 177.19(s), 176.21(s), 174.14(s), 171.04(s), 170,89(s), 166.38(d), 162.07(s), 134.95(s), 117.55(s), 79.68(s), 72.84(d), 67.09(t), 66.00(d), 63.90(t), 63.10(t), 59.00(d), 57.41(d), 57.36(d), 56.37(d), 42.25(t), 41.41(t), 35.35(t), 32.77(t), 31.47(t), 29.20(t), 28.60(t), 24.94(t), 23.49(t).

(9) Amino acid analysis: (the same conditions as those of A)
Serine (about 2 moles) and α-amino-adipic acid were detected.

(10) TLC: (the same conditions as those of A)
Rf=0.47

(11) HPLC: (the same conditions as those of A)
Rt=2.8 (min.)

(iii) TAN-591C.trihydrochloride
(1) Appearance: white powder
(2) Molecular weight: SIMS method, (M+H)$^+$834
(3) Molecular formula: $C_{32}H_{51}N_9O_{15}S.3HCl.(4H_2O)$
(4) Elemental analysis (%)

| Found*$^1$ | Calcd.*$^2$ |
|---|---|
| C, 36.74 ± 2.0 | C, 37.85 |
| H, 6.31 ± 1.0 | H, 6.16 |
| N, 11.74 ± 1.5 | N, 12.42 |
|  | O, 29.94 |
| S, 3.48 ± 1.0 | S, 3.16 |
| Cl, 11.86 ± 1.5 | Cl, 10.48 |

*$^1$The same conditions as those of A.
*$^2$The sample contains 4 mole of water.

(5) UV spectrum $\lambda_{max}^{H2O}$260±2 nm ($E_{1cm}^{1\%}$=110±20)

(6) CD spectrum:

$[\theta]_{226\pm2}^{H2O}$ −57000±5000 and $[\theta]_{258\pm2}^{H2O}$ +39000±5000

(7) IR spectrum:
3440, 3270, 3080, 2950, 1780, 1740, 1675, 1530, 1410, 1250, 1150, 1060, 960, 800, 540.

(8) Amino acid analysis: (the same conditions as those of A)
Serine (about 2 moles), alanine and α-amino-adipic acid were detected.

(9) TLC: (the same conditions as those of A)
Rf=0.51

(10) HPLC: (the same conditions as those of A)
Rt=3.3 (min.)

In said properties, the absolute configurations of serine, alanine and α-aminoadipic acid were determined by HPLC method as the L-form, L-form and D-form, respectively.

EXAMPLE 1

TAN-547 A (1.0 g) was dissolved in 0.02M aqueous disodium hydrogenphosphate solution (200 ml), and the solution was adjusted to pH 9.4 with 2N aqueous sodium hydroxide solution. The solution was stirred at room temperature for 33 hours, while adding 2N sodium hydroxide to the solution every 5 hours so that the pH might be maintained at 9.0 to 9.4. Water (100 ml) was added to the reaction solution, which was adjusted to pH 7.0, and the passed through a column packed with QAE Sephadex A-25 (Cl$^-$ type, 100 ml) (Pharmacia Fine Chemicals, Sweden), followed by elution and fractionation with 0.02M phosphate buffer (pH 7.0). The eluted fraction was subjected to an analysis of HPLC and the fractions showing a single peak were collected, and adjusted to pH 7.0. The collected solution was passed through a column packed with activated carbon (50 ml), and the column was washed with water (150 ml), followed by elution with 8% isobutanol (30 ml). The eluate was concentrated and lyophilized to give a white powder (253 mg) of 7-FA-DCPC sodium salt.

EXAMPLE 2

In 8.5 ml of 0.02M disodium hydrogenphosphate was dissolved 8.5 mg of TAN-547 B, and the solution was adjusted to pH 9.4 with 0.1N sodium hydroxide. The solution was stirred at room temperature for 24 hours, while adding 0.1N sodium hydroxide to the solution so that the pH might be maintained at 9.0 to 9.5. The reaction solution was subjected to an analysis of HPLC, whereby 1.3 mg of 7-FA-DCPC sodium salt was found to be produced. The physico-chemical properties indicated that the product was identical to the compound obtained in Example 1.

EXAMPLE 3

In 7 ml of 0.02M disodium hydrogenphosphate was dissolved 7.0 mg of TAN-547 C, and the solution was adjusted to pH 9.4 with 0.1N sodium hydroxide. The solution was stirred at room temperature for 24 hours, while adding 0.1N sodium hydroxide to the solution so that the pH might be maintained at 9.0 to 9.4. The reaction solution ws subjected to an analysis of HPLC, whereby 1.0 mg of 7-FA-DCPC sodium salt was found to be produced. The physico-chemical properties indicated that the product was identical to the compound obtained in Example 1.

EXAMPLE 4

After 7.2 g of disodium hydrogenphosphate was added to an aqueous solution (2 l, TAN-547 A, 9 g; TAN-547 B,8 g; TAN-547 C, 1.5 g) of a mixture of TAN-547 A, B and C, the solution was adjusted to pH 9.4 with 2N sodium hyroxide, and stirred at room temperature for 24 hours, while adding 2N sodium hydroxide to the solution so that the pH might be maintained at 9.0 to 0.4. Water (4 l) was added to the reaction solution, which was adjusted to pH 7.0 and passed through a column packed with QAE-Sephadex A-25 (Cl⁻ type, 2 l). The column was washed with water (3 l), and elution was performed with 0.03M phosphate buffer (ph 7.0) (8 l). The effluent was washing were combined and passed through a column of powdered charcoal (1 l), and the column was washed with water (4 l), followed by elution with 8% isobutanol (3 l). The eluate was concentrated, and the concentrate was passed through a column packed with Dowex 1×2 (Cl⁻ type, 50 to 100 mesh, 0.5 l). The column was washed with water (1 l), and elution was performed with 0.1M aqueous sodium chloride solution (2.5 l). The eluate and the eluate (8 l) from the above-mentioned QAE-Sephadex A-25 were combined and passed through a column packed with powdered charcoal (0.7 l), and the column was washed with water (2 l), followed by elution with 8% isobutanol (2.8 l). The eluate was concentrated, and the concentrate was lyophilized to give a powder of 7-FA-DCPC sodium salt (3.0 g). The physico-chemical properties showed that the product was identical to the compound obtained in Example 1.

EXAMPLE 5

TAN-547 D (90 mg) was dissolved in 0.01M aqueous disodium hydrogenphosphate solution (20 ml), and the solution was adjusted to pH 9.4 with 1N sodium hydroxide, and stirred at room temperature for 33 hours, while adding 0.1N sodium hydroxide every 5 hours so that the pH might be maintained at 9.0 to 9.4. Water (20 ml) was added to the reaction solution, which was adjusted to pH 7.0 and passed through a column packed with QAE-Sephadex A-25 (Cl⁻ type, 15 ml), followed by elution and fractionation with 0.02M phosphate buffer (pH 7.0). The eluted fraction was subjected to an analysis of HPLC, and the eluates showing a single peak were collected and adjusted to pH 7.0. The collected solution was passed through a column packed with activated carbon (10 ml), and the column was washed with water (40 ml), followed by elution with 8% isobutanol (70 ml). The eluate was concentrated and the concentrate was lyophilized to give a white powder (18 mg) of DCPC sodium salt.

EXAMPLE 6

In 3.8 ml of 0.02M disodium hydrogenphosphate was dissolved 7.0 mg of TAN-547 E, and the solution was adjusted to pH 9.4 with 0.2N sodium hydroxide, and stirred at room temperature for 32 hours, while adding 0.1N sodium hydroxide to the solution so that the pH might be maintained at 9 to 9.5. The rection solution was subjected to an analysis of liquid chromatography, whereby 1.4 mg of DCPC sodium salt was found to be produced. The physico-chemical properties indicated that the product was identical to the compound obtained in Example 5.

EXAMPLE 7

In 3.8 ml of 0.02M disodium hydrogenphosphate was dissolved 3.5 mg of TAN-547 F, and the solution was adjusted to pH 9.4 with 0.2N sodium hydroxide, and stirred at room temperature for 32 hours, while adding 0.1N sodium hydroxide to the solution so that the pH might be maintained at 9 to 9.5. The reaction solution was subjected to an analysis of liquid chromatography, whereby 0.64 mg of DCPC sodium salt was found to be produced. The physico-chemical properties showed that the product was identical to the compound obtained in Example 5.

EXAMPLE 8

In 10 ml of 0.02M disodium hydrogenphosphate were 4.3 mg of TAN-547 D, 3.6 mg of TAN-547E and 2.7 mg of TAN-547 F, and the solution was adjusted to pH 9.4 with 0.1N sodium hydroxide, and stirred at room temperature for 25 hours, while adding 0.1N sodium hydroxide to the solution so that the pH might be maintained at 9.0 to 9.5. The reaction solution was subjected to an analysis of HPLC, whereby 1.7 mg of DCPC sodium salt was found to be produced. The physico-chemical properties indicated that the product was identical to the compound obtained in Example 5.

EXAMPLE 9

TAN-592 A (0.5 g) was dissolved in 0.02M aqueous disodium hydrogenphosphate solution (100 ml), and the solution was adjusted to pH 9.5 with 2N aqueous sodium hydroxide solution, and stirred at room temperature for 30 hours, while maintaining the pH of the solution at 9.4 to 9.6. water (50 ml) was added to the reaction solution, which was adjusted to pH 7.0 and passed through a column packed with QAE Sephadex A-25 (Cl⁻ type, 50 ml), followed by elution and fractionation with 0.02M phosphate buffer (pH 7.0). The eluted fraction was subjected to an analysis of HPLC and the fractions showing signal peak were collected and adjusted to pH 7.0. The collected solution was passed through a column packed with activated carbon (25 ml), and the column was washed with water (75 ml), followed by elution with 8% isobutanol (150 ml). The eluate was concentrated, and the concentrate was lyophilized to give a white powder (112 mg) of 7-FA-DCPC sodium salt.

EXAMPLE 10

TAN-592 B (0.5 g) was dissolved in 0.02M aqueous disodium hydrogenphosphate solution (100 ml), and the solution was adjusted to pH 9.4 with 2N aqueous sodium hydroxide solution and stirred at room temperature for 32 hours, while maintaining the pH of the solution at 9.2 to 9.6. Water (50 ml) was added to the reaction solution, which was adjusted to pH 7.0 and passed through a column packed with QAE Sephadex A-25 (Cl⁻ type, 50 ml), followed by elution and fractionation with 0.02M phosphate buffer (pH 7.0). The eluted fraction was subjected to an analysis of HPLC, and the fractions showing a single peak were collected and adjust to pH 7.0. The collected solution was passed through a column packed with activated carbon (25 ml), and the column was washed with water (75 ml), followed by elution with 8% isobutanol (150 ml). The eluate was concentrated, and the concentrate was lyophilized to give a white powder (56 mg) of 7-FA-DCPC sodium salt.

EXAMPLE 11

In 8.0 ml of 0.02M disodium hydrogenphosphate was dissolved 8.0 mg of TAN-592 C, and the solution was adjusted to pH 9.4 with 0.1N sodium hydroxide, and stirred at room temperature for 20 hours, while adding 0.1N sodium hydroxide to the solution so that the pH might be maintained at 9.2 to 9.7. The reaction solution was subjected to an analysis of HPLC, whereby 1.1 mg of 7-FA-DCPC sodium salt was found to be produced. The physico-chemical properties indicated that the product was identical to the compound obtained in Example 9.

EXAMPLE 12

After 7.2 g of disodium hydrogenphosphate was added to an aqueous solution (2 l, TAN-592 A, 10.2 g; TAN-592 B, 8.2 g; TAN-592 C, 1.6 g) of a mixture of TAN-592 A, B and C, the solution was adjusted to pH 9.4 with 2N sodium hydroxide, and stirred at room temperature for 31 hours, while adding 2N sodium hydroxide to the solution so that the pH might be maintained at 9.0 to 9.4. Water (4 l) was added to the reaction solution, which was adjusted to pH 6.7 and passed through a column packed with Dowex 50W×2 (Na⁺ type, 1 l), followed by washing with water (1 l). The effluent and water washing were combined and passed through a column of powdered charcoal (1.5 l), and the column was washed with water (4 l), followed by elution with 8% isobutanol (7.5 l). The eluate was concentrated, and the concentrate was passed through a column packed with QAE-Sephadex A-25 (Cl⁻ type, 1 l), followed by elution and fractionation with 0.02M aqueous sodium chloride solution. The fraction (4 l) containing the antibiotic was passed through a column packed with powdered charcoal (1.5 l), and the column was washed with water (4.5 l), followed by elution with 8% isobutanol (4.5 l). The eluate was concentrated, and the concentrate was lyophilized to give a powder of 7-FA-DCPC sodium salt (4.1 g). The physico-chemical properties showed that the product was identical to the compound obtained in Example 9.

EXAMPLE 13

TAN-591 A (10 g) was dissolved in 0.02M aqueous disodium hydrogenphosphate solution (200 ml), and the solution was adjusted to pH 9.4 with 2N aqueous sodium hydroxide solution, and stirred at room temperature for 33 hours, while maintaining the pH of the solution at 9.0 to 9.4. Water (100 ml) was added to the reaction solution, which was adjusted to pH 7.0 and passed through a column packed with QAE Sephadex A-25 (Cl⁻ type, 100 ml), followed by elution and fractionation with 0.02M phosphate buffer (pH 7.0). The eluted fraction was subjected to an analysis of high-speed liquid chromatography, and the fractions showing a single peak were collected and adjusted to pH 7.0. The collected solution was passed through a column packed with activated carbon (50 ml), and the column was washed with water (150 ml), followed by elution with 8% isobutanol (300 ml). The eluate was concentrated, and the concentrate was lyophilized to give a white powder (122 mg) of 7-FA-DCPC sodium salt.

EXAMPLE 14

In 9.2 ml of disodium hydrogenphosphate was dissolved 9.2 mg of TAN-591 B, and the solution was adjusted to pH 9.4 with 0.1N sodium hydroxide, and stirred at room temperature for 20 hours, while adding 0.1N sodium hydroxide to the solution so that the pH might be maintained at 9.2 to 9.7. The reaction solution was subjected to an analysis of high-speed liquid chromatography, whereby 1.5 mg of 7-FA-DCPC was found to be produced. The physico-chemical properties indicated that the product was identical to the compound obtained in Example 9.

EXAMPLE 15

In 7.8 ml of 0.02M disodium hydrogenphosphate was dissolved 7.8 mg of TAN-591 C, and the solution was adjusted to pH 9.4 with 0.1N sodium hydroxide, and stirred at room temperature for 20 hours, while adding 0.1N sodium hydroxide to the solution so that the pH might be maintained at 9.2 to 9.7. The reaction solution was subjected to an analysis of high-speed liquid chromatography, whereby 0.82 mg of 7-FA-DCPC sodium salt was found to be produced. The physico-chemical properties indicated that the product was identical to the compound obtained in Example 9.

EXAMPLE 16

After 180 mg of disodium hydrogenphosphate was added to an aqueous solution (50 ml, TAN-591 A, 400 mg; TAN-591 B, 112 mg; TAN-591 C, 53 mg) of a mixture of TAN-591 A, B and C, the solution was adjusted to pH 9.4 with 2N sodium hydroxide, and stirred at room temperature for 24 hours, while adding 2N sodium hydroxide to the solution so that the pH might be maintained at 9.0 to 9.4. Water (100 ml) was added to the reaction solution, which was adjusted to pH 7.0 and passed through a column packed with Dowex 50W×2 (Na⁺ type, 25 ml), followed by washing with water (25 ml). The effluent and water washing was combined and passed through a column of powdered charcoal (25 ml), and the column was washed with water (100 ml), followed by elution with 8% isobutanol (75 ml). The eluate was concentrated, and the concentrate was passed through a column packed with QAE-Sephadex A-25 (Cl$^-$ type, 25 ml), followed by elution and fractionation with 0.02M aqueous sodium chloride solution (350 ml). The fraction (100 ml) containing the antibiotic was passed through a column packed with powdered charcoal (40 ml), and the column was washed with water (120 ml), followed by elution with 8% isobutanol (120 ml). The eluate was concentrated, and the concentrate was lyophilized to give a powder of 7-FA-DCPC sodium salt (140 mg). The physico-chemical properties showed that the product was identical to the compound obtained in Example 9.

EXAMPLE 17

TAN-592 D (100 mg) was dissolved in 0.01M aqueous disodium hydrogenphosphate solution (20 ml), and the solution was adjusted to pH 9.4 with 1N sodium hydroxide, and stirred at room temperature for 30 hours, while maintaining the pH of the solution at 9.0 to 9.4. Water (20 ml) was added to the reaction solution, which was adjusted to pH 7.0 and passed through a column of QAE-Sephadex A-25 (Cl$^-$ type, 15 ml), followed by elution and fractionation with 0.02M phosphate buffer (pH 7.0). The eluted fraction was subjected to an analysis of HPLC, and the fractions showing a single peak were collected and adjusted to pH 7.0. The collected solution was passed through a column packed with activated carbon (10 ml), and the column was washed with water (40 ml), followed by elution with 8% isobutanol (70 ml). The eluate was concentrated, and the concentrate was lyophilized to give a white powder (21 mg) of DCPC sodium salt.

EXAMPLE 18

In 9.2 ml of 0.02M disodium hydrogenphosphate was dissolved 9.2 mg of TAN-592 E, and the solution was adjusted to pH 9.4 with 0.2N sodium hydroxide, and stirred at room temperature for 20 hours, while adding 0.1N sodium hydroxide to the solution so that the pH might be maintained at 9.2 to 9.7. The reaction solution was subjected to an analysis of liquid chromatography, whereby 2.4 mg of DCPC sodium salt was found to be produced. The physico-chemical properties showed that the product was identical to the compound obtained in Example 17.

EXAMPLE 19

In 16 ml of 0.02M disodium hydrogenphosophate was dissolved 8.0 mg of TAN-592 F, and the solution was adjusted to pH 9.4 with 0.2N sodium hydroxide, and stirred at room temperature for 20 hours, while adding 0.1N sodium hydroxide to the solution so that the pH might be maintained at 9.2 to 9.7. The reaction solution was subjected to an analysis of liquid chromatography, whereby 2.0 mg of DCPC sodium salt was found to be produced. The physico-chemical properties indicated that the product was identical to the compound obtained in Example 17.

EXAMPLE 20

In 10 ml of 0.02M disodium hydrogenphosphate were 3 mg of TAN-592 D, 3 mg of TAN-592 E and 3 mg of TAN-592 F, and the solution was adjusted to pH 9.4 with 0.1N sodium hydroxide, and stirred at room temperature for 25 hours, while adding 0.1N sodium hydroxide to the solution so that the pH might be maintained at 9.0 to 9.5. The reaction solution was subjected to an analysis of high-speed liquid chromatography, whereby 1.5 mg of DCPC sodium salt was found to be produced. The physico-chemical properties showed that the product was identical to the compound obtained in Example 17.

EXAMPLE 21

*Trigonopsis variabilis* IFO 0755 was used to inoculate 200 ml flask containing 40 ml of a seed culture medium composed of the following components. Components of seed culture medium (pH 6.0) in 1 liter: 20 g of glucose, 4 g of KH$_2$PO$_4$, 1 g of MgSO$_4$.7H$_2$O, 0.5 g of CaCl$_2$, 0.1 g of H$_3$BO$_4$, 40 mg of (NH$_4$)$_6$Mo$_7$O$_{24}$.4H$_2$O, 40 mg of MnSO$_4$.4H$_2$O, 40 mg of ZnSO$_4$.7H$_2$O, 45 mg of CuSO$_4$.5H$_2$O, 25 mg of FeSO$_4$.7H$_2$O, 4 mg of thiamine hydrochloride, 20 μg of biotin, 4 g of DL-α-alanine. Shake culture was carried out at 28° C. for two days.

One ml of the culture broth was transferred into a main culture medium (the same components except that the medium contains DL-methionine in place of DL-α-alanine), and shake culture was carried out at 28° C. for 3 days. The cells were collected by high speed centrifugation, and washed with distilled water. The washed cells were dispersed into 40 ml of a solution of 1M pyrophosphate buffer (pH 8.0) to which had been previously added 10 mM of sodium azide. To the suspension was added 4 ml of an aqueous solution containing 440 mg of the compound (IV). The mixture was poured into 200 ml Erlenmeyer flask, and the reaction was carried out at 28° C. for 16 hours. The cells were removed by high speed contrifugation to give 91 ml of supernatant.

To the supernatant was added 500 ml of water and pH of the solution was adjusted to 7.0. The solution was passed through a column packed with 200 ml of QAE Sephadex A-25 (Cl$^-$ form), and the active fractions were eluted with 0.05M phosphate buffer (pH 7.0). The active portions were collected, and the portions were passed through a column packed with 200 ml of activated carbon. After washing the column with water, the active fractions were eluted with 1000 ml of 8% aqueous isobutanol and then 400 ml of 8% aqueous isobutanol-N/100 aqueous ammonia. The eluates were concentrated, the concentrate was passed through the column packed with QAE Sephadex A-25 (Cl$^-$ form, 200 ml), and the column was eluted with 0.03M phosphate buffer (pH 7.0). The respective eluate fractions were subjected to analysis of HPLC, and the fractions which shows a single peak were collected. The fractions were passed through a column of 300 ml of activated carbon. After washing the column with water (900 ml), elution was carried out with 900 ml of 8% aqueous isobutanol and then with 500 ml of 8% isobutanol-N/100 aqueous ammonia. The eluates were collected, concentrated and freeze-dried to give 360 mg of disodium salt of the compound (III).

EXAMPLE 22

One loopful of Pseudomonas sp. UK-2221 (IFO 14366, FERM BP-637) was subjected to inoculation to 200 ml of a culture medium composed of 1% peptone, 0.5% meat extract, 0.1% yeast extract, 0.05% glutaric acid, 0.5% NaCl (pH 10.0) which was previously poured into 1 liter Erlenmayer flask. The cultivation was carried out at 30° C. for 7 days under shaking.

Cells were collected by centrifugation, and the cells were suspended in 0.1M potassium phosphate buffer (pH 7.0) so as to be a concentration of 500 mg/ml. The suspension (20 ml) and 60 ml of 0.1M potassium phosphate buffer containing the compound (III) obtained the aforementioned Example 21 at a concentration of 15 mg/ml were mixed and the reaction was carried out at 37° C. for 48 hours by standing. The reaction mixture was subjected to centrifugation to remove the cells, and after the pH of the supernatant was adjusted to 7.2, the supernatant was subjected to column chromatography using 5 ml of activated carbon. After washing the column with water (10 ml), the active fractions were eluted with water (10 ml), and then 8% isobutyl alcohol (40 ml). The eluate was concentrated under reduced pressure, and the concentrate (1 ml) was passed through the column packed with 5 ml of QAE-Sephadex A-25 (Cl form). After washing the column with water (25 ml) and then with 0.02M NaCl-water (25 ml), the column was eluted with 0.05M NaCl-water to give 5 ml portions. Thus obtained portions were subjected to analysis of HPLC, and portions which shows a single peak of the objective compound were collected to give 20 ml of the active portions. The pH of the active portions was subjected to 6.9, and the portions were subjected to column chromatography of 5 ml of activated carbon. After washing the column with water (25 ml), the column was eluted with 8% aqueous isobutyl alcohol (25 ml) and then 8% aqueous isobutyl alcohol-N/100 aqueous ammonia (25 ml). The eluate was concentrated under reduced pressure, and freeze-dried, whereby 8.5 mg of free form of the compound (II) was obtained as white powders.

What we claim is:
1. A compound of the formula:

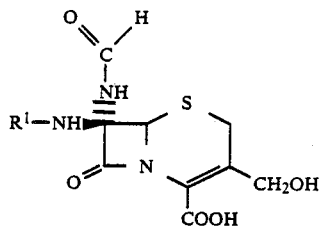

wherein $R^1$ is

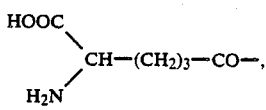

HOOC—$(CH_2)_3$—CO— or hydrogen, or a pharmaceutically acceptable salt thereof.

2. A compound as claimed in claim 1, wherein $R^1$ is

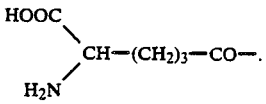

3. A compound as claimed in claim 1, wherein $R^1$ is HOOC—$(CH_2)_3$—CO—.

4. A compound as claimed in claim 1, wherein $R^1$ is hydrogen.

* * * * *